United States Patent
Erno et al.

(10) Patent No.: US 11,414,595 B2
(45) Date of Patent: Aug. 16, 2022

(54) ELECTROCHROMIC COMPOUNDS AND DEVICES

(71) Applicant: Gentex Corporation, Zeeland, MI (US)

(72) Inventors: Zachary B. Erno, Hudsonville, MI (US); Punam Giri, Holland, MI (US)

(73) Assignee: GENTEX CORPORATION, Zeeland, MI (US)

(*) Notice: Subject to any disclaimer, the term of this patent is extended or adjusted under 35 U.S.C. 154(b) by 249 days.

(21) Appl. No.: 16/890,071

(22) Filed: Jun. 2, 2020

(65) Prior Publication Data

US 2020/0379309 A1 Dec. 3, 2020
US 2021/0318584 A9 Oct. 14, 2021

Related U.S. Application Data

(60) Provisional application No. 62/856,321, filed on Jun. 3, 2019.

(51) Int. Cl.
| | |
|---|---|
| *G02F 1/1516* | (2019.01) |
| *C07D 405/14* | (2006.01) |
| *C09K 9/02* | (2006.01) |
| *G02F 1/1514* | (2019.01) |

(52) U.S. Cl.
CPC .............. *C09K 9/02* (2013.01); *C07D 405/14* (2013.01); *G02F 1/1516* (2019.01); *C09K 2211/104* (2013.01); *C09K 2211/1048* (2013.01); *G02F 2001/15145* (2019.01)

(58) Field of Classification Search
None
See application file for complete search history.

(56) References Cited

U.S. PATENT DOCUMENTS

| | | |
|---|---|---|
| 4,902,108 A | 2/1990 | Byker |
| 5,818,625 A | 10/1998 | Forgette et al. |
| 5,928,572 A | 7/1999 | Tonar et al. |
| 5,940,201 A | 8/1999 | Ash et al. |
| 5,998,617 A | 12/1999 | Srinivasa et al. |
| 6,020,987 A | 2/2000 | Baumann et al. |
| 6,188,505 B1 | 2/2001 | Lomprey et al. |
| 6,445,486 B1 | 9/2002 | Lomprey et al. |
| 6,597,489 B1 | 7/2003 | Guarr et al. |
| 6,635,194 B2 | 10/2003 | Kloeppner et al. |
| 6,700,692 B2 | 3/2004 | Tonar et al. |
| 6,710,906 B2 | 3/2004 | Guarr et al. |
| 7,428,091 B2 | 9/2008 | Baumann et al. |
| 9,964,828 B2 | 5/2018 | Theiste et al. |

*Primary Examiner* — Jay Yang
*Assistant Examiner* — J. L. Yang
(74) *Attorney, Agent, or Firm* — Price Heneveld LLP; Brian James Brewer

(57) ABSTRACT

An electro-optic element includes a first substrate defining first and second surfaces and a second substrate defining third and fourth surfaces. A first electrically conductive layer is disposed on the second surface and a second electrically conductive layer is disposed on the third surface. An electrochromic medium is disposed in a cavity between the first and second substrates, the electrochromic medium including an anodic component and a cathodic component. At least the anodic component is configured to reversibly attenuate transmittance of light having a wavelength within a predetermined wavelength range when in an electrochemically activated state. The anodic component includes a substituted ketal phenazine compound.

20 Claims, 8 Drawing Sheets

Compound (I)

ELECTROCHROMIC COMPOUNDS AND DEVICES

CROSS-REFERENCE TO RELATED APPLICATION

This application claims priority to and the benefit under 35 U.S.C. § 119(e) of U.S. Provisional Application No. 62/856,321, filed on Jun. 3, 2019, entitled ELECTROCHROMIC COMPOUNDS AND DEVICES, the disclosure of which is hereby incorporated herein by reference in its entirety.

FIELD OF THE DISCLOSURE

The present disclosure generally relates to electrochromic compounds for electro-optic elements and mediums, and more particularly to substituted ketal phenazines suitable for use as an electrochromic component.

SUMMARY OF THE DISCLOSURE

According to one aspect of the present disclosure, an electro-optic element includes a first substrate defining first and second surfaces, wherein a first electrically conductive layer is disposed on the second surface, and a second substrate defining third and fourth surfaces, wherein a second electrically conductive layer is disposed on the third surface. An electrochromic medium is disposed in a cavity between the first and second substrates, the electrochromic medium including an anodic component and a cathodic component. At least the anodic component is configured to reversibly attenuate transmittance of light having a wavelength within a predetermined wavelength range when in an electrochemically activated state. The anodic component comprises a compound of Formula (I):

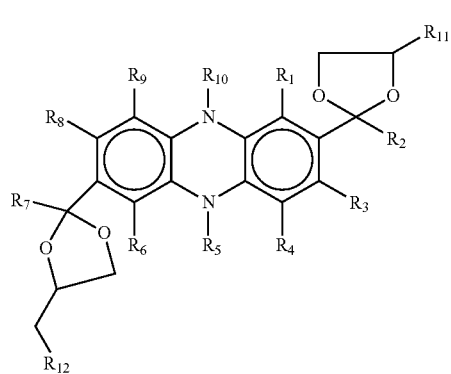

(I)

wherein $R_1$, $R_2$, $R_3$, $R_4$, $R_6$, $R_7$, $R_8$, $R_9$, $R_{11}$, and $R_{12}$ are individually a hydrogen, an alkyl, a substituted alkyl, a straight chain alkyl, a branched alkyl, or a cycloalkyl and $R_5$ and $R_{10}$ are individually an alkyl, a substituted alkyl, a straight chain alkyl, a branched alkyl, or a cycloalkyl.

According to an aspect of the present disclosure, a medium for an electro-optic element includes an anodic component configured to reversibly attenuate transmittance of light having a wavelength within a predetermined wavelength range when in an electrochemically activated state, wherein the anodic component comprises a compound of Formula (I):

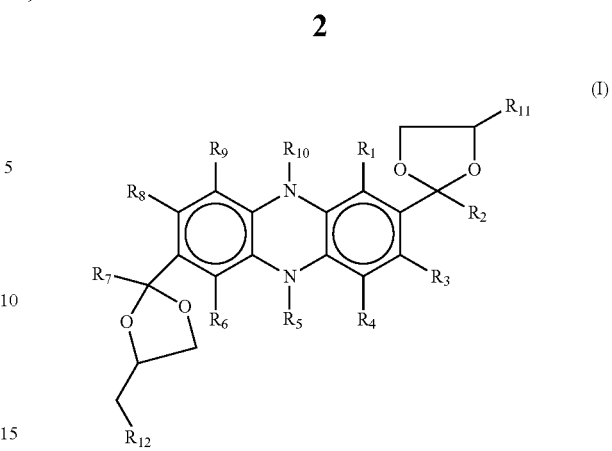

(I)

wherein $R_1$, $R_2$, $R_3$, $R_4$, $R_6$, $R_7$, $R_8$, $R_9$, $R_{11}$, and $R_{12}$ are individually a hydrogen, an alkyl, a substituted alkyl, a straight chain alkyl, a branched alkyl, or a cycloalkyl and $R_5$ and $R_{10}$ are individually an alkyl, a substituted alkyl, a straight chain alkyl, a branched alkyl, or a cycloalkyl.

These and other features, advantages, and objects of the present disclosure will be further understood and appreciated by those skilled in the art by reference to the following specification, claims, and appended drawings.

DETAILED DESCRIPTION

Figure 1:
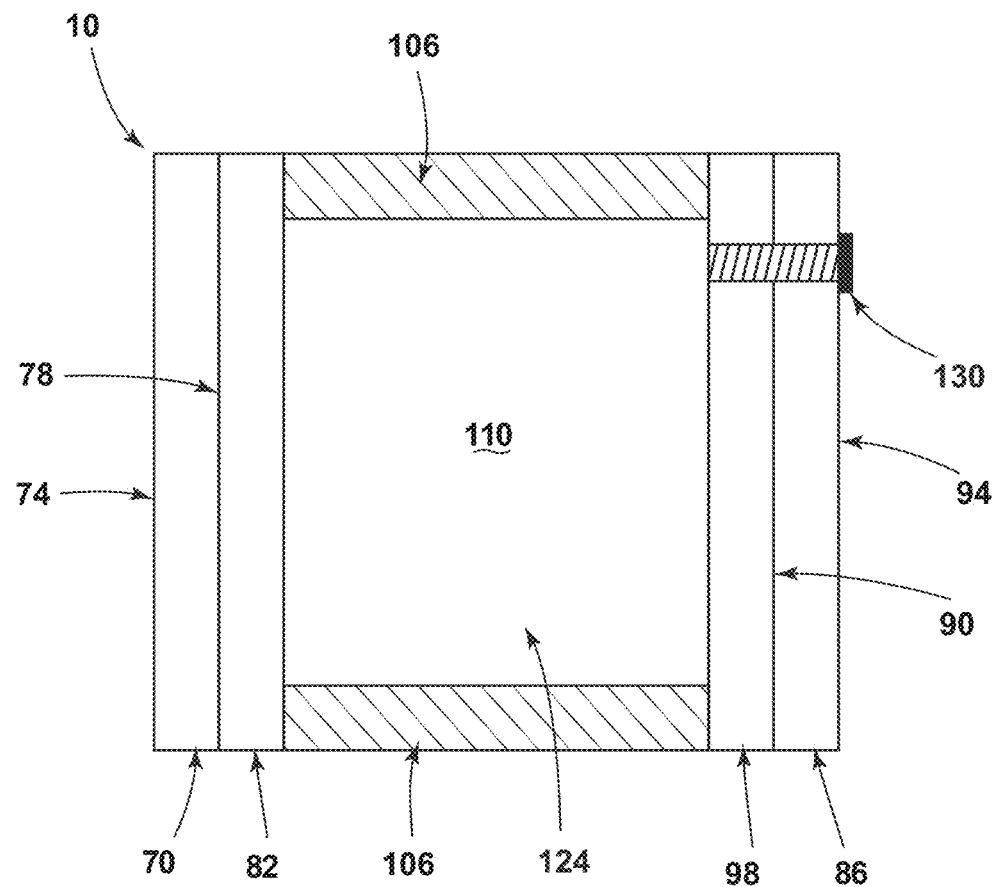
FIG. 1 is a cross-sectional schematic view of an electrochromic device including an electro-optic element, according to aspects of the present disclosure.

The present illustrated embodiments reside primarily in combinations of materials, method steps, and apparatus components relating to an electrochromic medium and electro-optic element that includes an anodic component configured to reversibly attenuate transmittance of light having a wavelength within a predetermined wavelength range when in an electrochemically activated state, the anodic component being a substituted ketal phenazine compound according to Formula (I), as discussed below. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

As used herein, the term "and/or," when used in a list of two or more items, means that any one of the listed items can be employed by itself, or any combination of two or more of the listed items, can be employed. For example, if a composition is described as containing components A, B, and/or C, the composition can contain A alone; B alone; C alone; A and B in combination; A and C in combination; B and C in combination; or A, B, and C in combination.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Aspects of the present disclosure relate to a family of electrochromic compounds capable of attenuating the transmittance of at least a portion of the electromagnetic spectrum. The electrochromic compounds of the present disclosure can be used in electro-optic elements and electrochromic devices incorporating such electro-optic elements. The electrochromic compounds of the present disclosure include a substituted ketal phenazine compound of Formula (I):

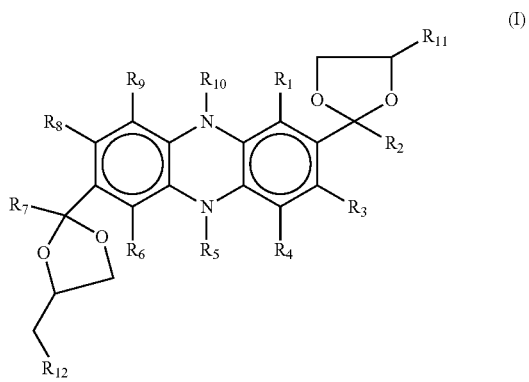

wherein $R_1$, $R_2$, $R_3$, $R_4$, $R_6$, $R_7$, $R_8$, $R_9$, $R_{11}$, and $R_{12}$ are individually a hydrogen, an alkyl, a substituted alkyl, a straight chain alkyl, a branched alkyl, or a cycloalkyl and $R_5$ and $R_{10}$ are individually an alkyl, a substituted alkyl, a straight chain alkyl, a branched alkyl, or a cycloalkyl. In some aspects, one of: (a) $R_5$ and $R_{10}$, (b) $R_{11}$ and $R_{12}$, or (c) a combination of $R_5$, $R_{10}$, $R_{11}$, and $R_{12}$ are individually an alkyl, a substituted alkyl, a straight chain alkyl, a branched alkyl, or a cycloalkyl substituted with at least one polymerizable functional group.

The substituted ketal phenazine compounds of Formula (I) are electrochromic and electroactive and thus can be used as an anodic component in combination with a cathodic component to form electro-optic elements that can be incorporated into electrochromic devices. By way of introduction, electrochromic devices generally include an electrochromic medium that transitions between an inactivated state in which the electrochromic medium is relatively transparent to light having a wavelength within a predetermined wavelength range and an activated state in which the electrochromic medium has a decreased transmission to light within a predetermined wavelength range when an electrical potential is applied to the electrochromic device. The electrochromic medium includes an anodic component and a cathodic component (also referred to as electroactive components), at least one of which is also electrochromic. The electrochromic electroactive component can provide the electrochromic device with a perceived color when the electrochromic device is in the activated state and/or as the device transitions between the inactivated and activated states. The term "electroactive," as used herein, refers to a material that can undergo a modification in its oxidation state upon exposure to a particular electrical potential difference. The term "electrochromic," as used herein, refers to a material that can exhibit a change in its extinction coefficient at one or more wavelengths upon exposure to a particular electrical potential difference. Electrochromic components, as described herein, include materials whose color or opacity are affected by an electrical current, such that when an electrical field is applied to the material, the color or opacity changes from a first state to a second state. Thus, an electrochromic device can exhibit a change in transparency as a result of electrochemical oxidation and reduction reactions that occur between electroactive components (i.e., the anodic components and the cathodic components), in which at least one of the electroactive components is also electrochromic.

In some applications, it may be desirable that the electrochromic device have a perceived neutral or gray color to an observer in the activated state and/or during the transition between the activated and inactivated states. For example, with respect to an electrochromic mirror or window assembly, it may be desirable that the assembly have a gray color in an activated state and/or during a transition between activated and inactivated states. A gray color in the activated state may be perceived by an observer as interfering less with the images visible in or through the assembly than other colors. Aspects of the present disclosure provide an anodic component in the form of the substituted ketal phenazine compound according to Formula (I) that can be used in combination with at least one additional anodic component to provide an electrochromic medium that appears more gray in color when activated compared to the color exhibited by either of the anodic components alone.

Referring to FIGS. 1 and 2A-E, reference numeral 10 generally designates an electrochromic device according to an aspect of the present disclosure. The electrochromic device 10 can include a first substrate 70 having a first surface 74 and a second surface 78, and a first electrically conductive layer 82 disposed on the second surface 78. A second substrate 86 is provided opposite the first substrate 70, and includes a third surface 90 and a fourth surface 94. A second electrically conductive layer 98 is disposed on the third surface 90. The first substrate 70 and the second substrate 86, along with a sealing member 106 define a chamber 110 for containing an electrochromic medium. The electrochromic device 10 can also include one or more plugs 130 associated with one or more fill ports. The one or more fill ports may be disposed within the first substrate 70, the second substrate 86, or the sealing member 106. Upon mounting as a mirror, window, filter, or other device, the electrochromic device 10 may optionally include a bezel (not shown) that extends around a periphery of at least one of the first substrate 70 and/or the second substrate 86 to conceal and/or protect components of the electrochromic device 10 and the like, such as a bus connector (if present), the sealing member 106, one or more plugs 130, and/or the one or more fill ports.

In some aspects, the first and second substrates 70, 86 may be larger than one another or the same in size, but shifted, to create an offset along at least a portion of the perimeter of the electrochromic device 10 to allow for easier access to the first and/or second electrically conductive layers 82, 98. The first and/or second substrates 70, 86 can be made of glass, plastic, or other optically transparent or translucent material, non-limiting examples of which include borosilicate glass, soda lime glass, or polymeric materials such as natural and synthetic polymeric resins, plastics, and/or composites including polyesters (e.g. PET), polyimides (PI), polycarbonates, polysulfones, polyethylene naphthalate (PEN), ethylene vinyl acetate (EVA), acrylate polymers, as well as cyclic olefin copolymers (COC) commercially available from TOPAS® Advanced Polymers. In some aspects, both the first and second substrates 70, 86 are made of an optically transparent or translucent material, while in other aspects, only the first substrate 70 is made of an optically transparent or translucent material. The first and second substrates 70, 86 can be made from the same or different materials and may have the same or different dimensions. According to some aspects, the second electrically conductive layer 98 may include a metal reflector or one or more coatings configured as a partially reflective, partially transmissive ("transflective") coating. Inclusion of a metal reflector or a transflective coating may render the electrochromic device 10 at least partially reflective.

The first and second electrically conductive layers 82, 98 can include one or more layers of an electrically conductive material disposed on the first and second substrates 70, 86, respectively. These layers serve as electrodes (i.e., the cathode and the anode) for the electrochromic device 10. The electrically conductive material(s) of the first and/or second electrically conductive layers 82, 98 may be any suitable material that includes one or more of the following features: (a) is substantially transparent to visible and/or IR light; (b) bonds reasonably well to the first and second substrates 70, 86; (c) maintains the bond to the first and second substrates 70, 86 when associated with a sealing member 106; (d) is generally resistant to corrosion from materials contained within the electrochromic device 10 or the atmosphere; and/or (e) exhibits minimal diffuse or specular reflectance as well as sufficient electrical conductance. Depending on the application, only one of the first and second electrically conductive layers 82, 98 may be required to be transparent while the other electrically conductive layer 82, 98 may be opaque. In some applications, both the first and the second electrically conductive layers 82, 98 may be transparent. The electrically conductive material(s) forming the first and second electrically conductive layers 82, 98 may be the same or different. Non-limiting examples of electrically conductive material that may be used to form the first and/or second electrically conductive layers 82, 98 can include fluorine doped tin oxide (FTO), for example TEC™ glass, indium tin oxide (ITO), doped zinc oxide, indium zinc oxide (IZO), aluminum doped zinc oxide (AZO), and metal oxide/metal/metal oxide (wherein the metal oxide can be substituted with metal carbide, metal nitride, metal sulfide, etc . . . ).

While aspects of the present disclosure are described in the context of the electrochromic device 10, aspects of the present disclosure may also be utilized in the context of other electrochromic devices, non-limiting examples of which include those disclosed in U.S. Pat. No. 5,818,625, issued Oct. 6, 1998 and entitled "Electrochromic Rearview Mirror Incorporating a Third Surface Metal Reflector,"; U.S. Pat. No. 6,597,489, issued Jul. 22, 2003 and entitled "Electrode Design for Electrochromic Devices,"; and U.S. Pat. No. 6,700,692, issued Mar. 2, 2004 and entitled "Electrochromic Rearview Mirror Assembly Incorporating a Display/Signal Light," all of which are incorporated herein by reference in their entirety including all references incorporated therein.

Still referring to FIGS. 1 and 2A-E, the electrochromic device 10 includes an electro-optic element 140 that is at least partially defined by the first and second substrates 70, 86, the chamber 110, and the electrochromic medium 124. The electro-optic element 140 allows the electrochromic device 10 to be operable between a transparent or clear state, which allows light having a wavelength within a predetermined wavelength range to pass through, and a darkened state, in which a portion, or no light having a wavelength within a predetermined wavelength range, is transmitted through the electro-optic element 140 (i.e., the electro-optic element 140 becomes essentially opaque or partially opaque to light having a wavelength within the predetermined wavelength range). The electro-optic element 140 may be operable between a substantially clear state and a substantially dark or darkened state, as well as intermediate states thereto. The darkened state of the electro-optic element 140 can be defined relative to the transmissivity of the substantially clear state. According to an aspect of the present disclosure, the transmissivity of the electro-optic element 140 in the substantially transparent or clear state may be greater than about 25%, greater than about 50%, greater than about 55%, or greater than about 85%. The percentage of reflectance, transmittance, and absorbance of the electro-optic element 140 sum to 100%. In some aspects, the transmissivity of the electro-optic element 140 in the substantially darkened state may be less than about 10%, less than about 1%, less than about 0.1%, less than about 0.01%, or less than about 0.001%.

The sealing member 106 can traverse an approximate perimeter of, and is configured to cooperate with, the first and second substrates 70, 86 to define the chamber 110 as substantially hermetic. The sealing member 106 may be applied to the first or second substrates 70, 86 by methods commonly used in the liquid crystal display (LCD) industry, such as by silk-screening or dispensing. In one example, the sealing member 106 may incorporate a first and a second seal as components of the sealing member 106. In one example, first and second annular bands of highly conductive material are optionally deposited around the perimeter of the first and second substrates 70, 86, respectively, and electrically-conducting structures (e.g., clips or wires) are secured to the highly conductive material and spatially separated from one another. The electrically-conducting structures may supply an electrical voltage to the first and second annular bands of highly conductive material to create a voltage across the electro-optic element 140, thereby reversibly driving the electro-optic element 140 between the substantially dark and substantially clear states. The first and second annular bands of highly conductive material may include silver, gold, copper, or aluminum (such as, for example, in a form of metallic flakes or particles dispersed in a hosting material).

Referring to FIGS. 2A-E, the electro-optic element 140 includes an electrochromic medium, at least one cathodic component, and at least one anodic component. The anodic and cathodic components may alternatively be referred to as chromophores or electrochromic molecules. According to some aspects of the present disclosure, the anodic and/or cathodic components may be a polymer and/or a monomer. In some aspects, both the cathodic and anodic components are electroactive and at least the anodic component is electrochromic.

According to an aspect of the present disclosure, the anodic component comprises a substituted ketal phenazine of Formula (I):

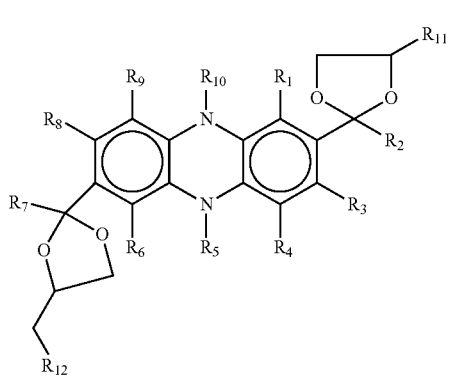

(I)

wherein $R_1$, $R_2$, $R_3$, $R_4$, $R_6$, $R_7$, $R_8$, $R_9$, $R_{11}$, and $R_{12}$ are individually a hydrogen, an alkyl, a substituted alkyl, a straight chain alkyl, a branched alkyl, or a cycloalkyl and $R_5$ and $R_{10}$ are individually an alkyl, a substituted alkyl, a straight chain alkyl, a branched alkyl, or a cycloalkyl. In some aspects, both $R_5$ and $R_{10}$, both $R_{11}$ and $R_{12}$, or a combination of $R_5$, $R_{10}$, $R_{11}$, and $R_{12}$ are individually an alkyl, a substituted alkyl, a straight chain alkyl, a branched alkyl, or a cycloalkyl substituted with at least one polymerizable functional group. For example, the polymerizable functional group can be a vinyl group, an acrylate group, a methacrylate group, a vinyl ether group, a hydroxyl group, an isocyanate group, an oxetane group, an amine group, and an epoxy group.

As used herein, "alkyl" groups include straight chain and branched alkyl groups having from 1 to 20 carbon atoms, from 1 to 12 carbon atoms, from 1 to 8 carbon atoms, from 1 to 6 carbon atoms, from 6 to 20 carbon atoms, from 6 to 12 carbon atoms, from 8 to 20 carbon atoms, or from 12 to 20 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term haloalkyl is an alkyl group having one or more halo groups. In some aspects, haloalkyl refers to a per-haloalkyl group. As used herein, $C_m$-$C_n$, such as $C_1$-$C_{12}$, $C_1$-$C_8$, or $C_1$-$C_6$, when used before a group refers to that group containing m to n carbon atoms.

As used herein, "substituted" refers to an alkyl group in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some aspects, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxya mines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like. Such substitution includes solubility enhancing groups as described in U.S. Pat. No. 6,445,486, issued Sep. 3, 2002.

Cycloalkyl groups are cyclic alkyl groups such as, but not limited to, cyclopropyl, cyclobutyl, cyclopentyl, cyclohexyl, cycloheptyl, and cyclooctyl groups. Cycloalkyl groups may be substituted or unsubstituted. Cycloalkyl groups further include polycyclic cycloalkyl groups such as, but not limited to, norbornyl, adamantyl, bornyl, camphenyl, isocamphenyl, and carenyl groups, and fused rings, non-limiting examples of which include decalinyl. Cycloalkyl groups also include rings that are substituted with straight or branched chain alkyl groups as defined above. Representative substituted cycloalkyl groups may be mono-substituted or substituted more than once, non-limiting examples of which include: 2,2-; 2,3-; 2,4-; 2,5-; or 2,6-disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

In some aspects, the substituted ketal phenazine of the present disclosure includes at least one substituent including a polymerizable functional group. Such polymerizable functional groups allow the substituted ketal phenazine to be covalently bonded to a polymeric matrix. In one example, one of: (a) a combination of $R_5$ and $R_{10}$, (b) a combination of $R_{11}$ and $R_{12}$, or (c) a combination of $R_5$, $R_{10}$, $R_{11}$, and $R_{12}$ include a polymerizable functional group. Non-limiting examples of suitable polymerizable functional groups include a vinyl group, an acrylate group, a methacrylate group, a vinyl ether group, a hydroxyl group, an isocyanate group, an oxetane group, an amine group, and an epoxy group. According to one aspect, a combination of both $R_5$ and $R_{10}$, a combination of both $R_{11}$ and $R_{12}$, or a combination of $R_5$, $R_{10}$, $R_{11}$, and $R_{12}$ can individually be a $C_1$-$C_{20}$ alkyl group including at least one substituted polymerizable functional group. For example, the alkyl group can include from 1 to 20 carbon atoms, from 1 to 12 carbon atoms, from 1 to 8 carbon atoms, from 1 to 6 carbon atoms, from 6 to 20 carbon atoms, from 6 to 12 carbon atoms, from 8 to 20 carbon atoms, or from 12 to 20 carbon atoms linking the polymerizable functional group with the substituted ketal phenazine. The alkyl group can be a straight chain alkyl, a branched alkyl, a cycloalkyl, or a substituted alkyl.

Figure 3A:
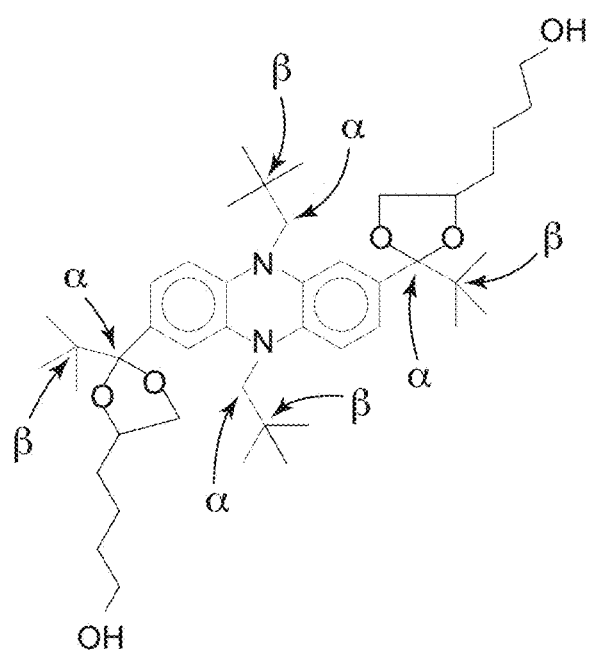
FIG. 3A illustrates the chemical structure of an exemplary electrochromic compound, according to an aspect of the present disclosure.
Figure 3B:
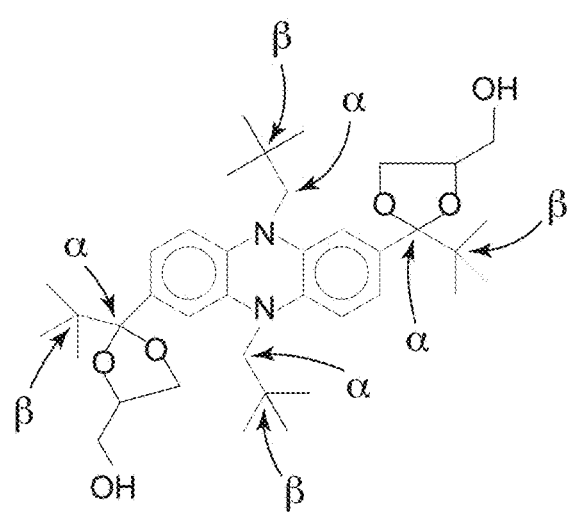
FIG. 3B illustrates the chemical structure of an exemplary electrochromic compound, according to an aspect of the present disclosure.

In some aspects of the present disclosure, at least one of the groups $R_2$, $R_5$, $R_7$, and $R_{10}$ is free of beta hydrogens. In one example, all of the groups $R_2$, $R_5$, $R_7$, and $R_{10}$ are free of beta hydrogens such that the substituted ketal phenazine according to Formula (I) is free of beta hydrogens. In one aspect, $R_5$ and $R_{10}$ are free of beta hydrogens, $R_2$ and $R_7$ are free of beta hydrogens, or $R_2$, $R_5$, $R_7$, and $R_{10}$ are all free of beta hydrogens. Neopentyl and 1-adamantane methyl are examples of substituent groups that are free of beta hydrogens. FIGS. 3A and 3B illustrate exemplary substituted ketal phenazine compounds, 4-(2-tert-butyl-2-{7-[2-tert-butyl-4-(4-hydroxylbutyl)-1,3-dioxolan-2-yl}-5,10-bis(2,2-dimethylpropyl) phenazine-2-yl)-1,3-dioxolan-4-yl}butane-1-ol ("Compound (I)") and 4-(2-tert-butyl-2-{7-[2-tert-butyl-4-(4-hydroxymethyl)-1,3-dioxolan-2-yl]-5,10-bis(2,2-dimethylpropyl) phenazine-2-yl}-1,3-dioxolan-4-yl) methanol ("Compound (II)"), according to Formula (I), in which the groups $R_5$, and $R_{10}$ are neopentyl groups and the groups $R_2$ and $R_7$ are tertiary alkyl groups, and thus Compounds I and II are both free of beta hydrogens. Compound (II) is similar to Compound (I) except that the alkyl chain coupling the hydroxyl functional group to the ketal includes fewer carbons. Without being limited by any theory, it is believed that the absence of beta hydrogens can increase a stability of the substituted ketal phenazine according to Formula (I), especially in applications in which the substituted ketal phenazine is exposed to ultraviolet (UV) light, such as in electrochromic windows and sunroofs, for example.

In some aspects of the present disclosure, the substituted ketal phenazines according to Formula (I) can be characterized by a maximum absorbance at about 400 nm to about 550 nm, when oxidized (i.e., when in the activated state). For example, the substituted ketal phenazines according to Formula (I) can be characterized by a maximum absorbance of about 410 nm to about 550 nm, about 420 nm to about 550 nm, about 430 nm to about 550 nm, about 440 nm to about 550 nm, about 450 nm to about 550 nm, about 460 nm to about 550 nm, about 470 nm to about 550 nm, about 480 nm to about 550 nm, about 490 nm to about 550 nm, 410 nm to about 500 nm, about 420 nm to about 500 nm, about 430 nm to about 500 nm, about 440 nm to about 500 nm, about 450 nm to about 500 nm, about 460 nm to about 500 nm, about 470 nm to about 500 nm, about 480 nm to about 500 nm, about 490 nm to about 500 nm, when oxidized. In one example, the substituted ketal phenazines according to Formula (I) can be characterized by a maximum absorbance of about 450 nm, about 455 nm, about 460 nm, about 465 nm, about 470 nm, about 475 nm, about 480 nm, about 485 nm, about 490 nm, about 500 nm, or any value between these values, when oxidized.

In some aspects of the present disclosure, the substituted ketal phenazines according to Formula (I) can be characterized by an oxidation potential of about 300 mV. For example, the substituted ketal phenazines according to Formula (I) can be characterized by an oxidation potential of about 270 mV to about 325 mV, about 275 mV to about 325 mV, about 280 mV to about 325 mV, about 285 mV to about 325 mV, about 290 mV to about 325 mV, about 295 mV to about 325 mV, about 300 mV to about 325 mV, about 305 mV to about 325 mV, about 310 mV to about 325 mV, about 270 mV to about 315 mV, about 275 mV to about 315 mV, about 280 mV to about 315 mV, about 285 mV to about 315 mV, about 290 mV to about 315 mV, about 295 mV to about 315 mV, about 300 mV to about 315 mV, about 305 mV to about 315 mV, 270 mV to about 300 mV, about 275 mV to about 300 mV, about 280 mV to about 300 mV, about 285 mV to about 300 mV, or about 290 mV to about 300 mV. In some examples, the substituted ketal phenazines according to Formula (I) can be characterized by an oxidation potential of about 270 mV, about 275 mV, about 280 mV, about 285 mV, about 290 mV, about 295 mV, about 300 mV, about 305 mV, about 310 mV, about 315 mV, about 320 mV, about 325 mV, or any value between these values.

In some aspects, an electrochromic medium according to an aspect of the present disclosure includes a substituted ketal phenazine according to Formula (I) in combination with at least one additional anodic component(s) such that when oxidized, the combination of anodic components exhibit a neutral gray color to an observer. For example, a substituted ketal phenazine according to Formula (I) can be combined with one or more additional anodic phenazine compounds such that when oxidized, the combination of anodic components exhibit a neutral gray color. The color of the electrochromic medium can be characterized using CIE LAB color coordinates. The CIE LAB color space defines the color of a material using the lightness value L* and color coordinates a* and b*. An L* value of 0 in CIELAB color space represents the darkest black and an L* value of 100 is indicative of the brightest white. The a* axis in color space is representative of the green-red color component, with negative a* values corresponding to green and positive a* values corresponding to red. The b* axis in color space is representative of the blue-yellow component, with negative b* values corresponding to blue and positive b* values corresponding to yellow. The closer the a* and b* values are to the origin, the more gray (i.e., neutral) in color the aperture structure will appear to an observer.

For example, an electrochromic medium according to an aspect of the present disclosure can include a substituted ketal phenazine according to Formula (I) in combination with at least one additional anodic component(s) such that when oxidized, the electrochromic medium is characterized by an a* value of about 0 to about ±25, about 0 to about ±20, about 0 to about ±15, about 0 to about ±10, or about 0 to about ±5 and a b* value of about 0 to about ±25, about 0 to about ±20, about 0 to about ±15, about 0 to about ±10, or about 0 to about ±5, when illuminated with a D65 series illuminant (representing natural daylight) at an angle of incidence (A01) of 2 degrees. In one example, the electrochromic medium is characterized by an a* and a b* value that are individually, about 0, about ±5, about ±10, about ±15, about ±20, about ±25, or any value between these values when illuminated with a D65 series illuminant and an AOI of 2 degrees.

In one aspect, an electrochromic medium according to an aspect of the present disclosure can include a substituted ketal phenazine according to Formula (I) in combination with at least one additional anodic component(s) and at least one electrochromic cathodic component such that when the electrochromic components are activated (i.e., the anodic components are oxidized and the cathodic components are reduced), the electrochromic medium is characterized by an a* value of about 0 to about ±25, about 0 to about ±20, about 0 to about ±15, about 0 to about ±10, or about 0 to about ±5 and a b* value of about 0 to about ±25, about 0 to about ±20, about 0 to about ±15, about 0 to about ±10, or about 0 to about ±5, when illuminated with a D65 series illuminant and an AOI of 2 degrees. In one example, the electrochromic medium is characterized by an a* and a b* value that are individually, about 0, about ±5, about ±10, about ±15, about ±20, about ±25, or any value between these values when illuminated with a D65 series illuminant and an AOI of 2 degrees. For example, a substituted ketal phenazine according to Formula (I) can be combined with at least one additional anodic phenazine and a cathodic viologen.

According to one aspect, an oxidation potential of the substituted ketal phenazine according to Formula (I) and the oxidation potential of each of the additional anodic component(s) are within ±60 mV. Selecting anodic components such that the oxidation potentials are near one another may facilitate achieving a consistent observable color appearance during darkening and clearing of the electrochromic device during operation. In some examples, an oxidation potential of the substituted ketal phenazine according to Formula (I) and an oxidation potential of each of the additional anodic component(s) can be selected to be within ±60 mV, within ±55 mV, within ±50 mV, within ±45 mV, or within ±40 mV.

The present substituted ketal phenazine compounds of Formula (I) can be utilized in solution form, gel form, or film form as the anodic component in an electrochromic medium of an electro-optic element. The electrochromic medium may include layers of materials attached directly to an electrically conductive layer or confined in close proximity to an electrically conductive layer which remains attached or confined when components thereof are oxidized and/or reduced.

In one aspect, the substituted ketal phenazine compounds of Formula (I) may be incorporated into a polymeric film to form an anodic film. The present substituted ketal phenazine compounds can be incorporated into the backbone of the polymeric chains forming the polymeric film and/or covalently bonded to the polymeric chains as pendant groups. For example, the anodic film may be a polymeric film including a plurality of polymeric chains composed of a number of repeating monomer units forming a backbone of the polymer chains. The cathodic film may include a binder polymer (e.g., polymethylmethacrylate, PMMA, polyvinyl formal, or polyethylene glycol), a plasticizer that will help facilitate ion conductivity (e.g., propylene carbonate or gamma-butyrolactone) and a supporting electrolyte (e.g., tetraethylammonium tetrafluoroborate or lithium hexafluorophosphate). The substituted ketal phenazine compounds of Formula (I) may form pendant groups attached to the polymer backbone or be disposed between the monomer units of the backbone.

According to one aspect, the substituted ketal phenazine compounds of Formula (I) can include a hydroxyl group, such that the compound may be bound into a polymer matrix via a condensation reaction or react with an isocyanate functionality to form a polyurethane-based polymer matrix. Amines may also react with isocyanate functionalities to form urea and biuret linkages. It is also within the scope of the present disclosure to utilize other polymeric matrix systems that contain compounds of Formula (I) that can be formed using a multi-functional epoxy in combination with a curing agent like an amine, alcohol, or anhydride or through base or acid catalyzed homo-polymerization. Non-limiting examples of materials that may be used as a polymeric matrix for covalently bonding with the substituted ketal phenazine compounds of Formula (I) include: polymethylmethacrylate, polypropylene methacrylate, polystyrene, polyurethanes, polyethers, polyesters, polycarbonates, polysiloxanes, polysilanes, polyacrylonitriles, polymethacrylonitriles, polyamides, polyimides, polyvinylidene halides, and co-polymer and combinations of thereof. Further examples of polymer matrix materials can be found in U.S. Pat. Nos. 6,635,194; 5,940,201; 5,928,572; and 9,964,828, which are herein incorporated by reference in their entirety.

In another aspect, the anodic film may be a solid polymer or a gel polymer. For example, the polymer may be an acrylate-based polymer that is dissolved in a solvent which incorporates the substituted ketal phenazine compounds of Formula (I). This solution is then coated on the conductive surface of a substrate, followed by removal of the solvent. The resultant film is an acrylate film that may be hard or tacky to the touch. In another example, the polymer film may be a gel that contains solvent as well as the substituted ketal phenazine compounds of Formula (I). Optionally, the polymer film maybe subsequently cross-linked for increased mechanical stability. Other non-limiting examples of polymer matrix systems that could be used with the substituted ketal phenazine compounds of Formula (I) include: polyacrylate, polymethacrylates, polyethers, polyesters, polycarbonates, polyurethanes, polysiloxanes, polysilanes, polyacrylonitriles, polystyrenes, polymethacrylonitriles, polyamides, polyimides, polyvinylidene halides, and co-polymers, or combinations of any two or more thereof. Further examples of polymer matrix materials used in electrochromic devices can be found in U.S. Pat. Nos. 6,635,194; 5,940,201; 5,928,572; and 9,964,828, which are herein incorporated by reference in their entirety.

The electrochromic medium can include one or more anodic components in addition to the substituted ketal phenazines of the present disclosure, examples of which include: metallocenes, 5,10-dihydrophenazines, phenothiazines, phenoxazines, carbazoles, triphenodithiazines, triphendioxazines, ferrocene, substituted ferrocenes, substituted ferrocenyl salts, phenazine, substituted phenazines, phenothiazine, substituted phenothiazines, including substituted dithiazines, thianthrene and substituted thianthrenes, di-tert-butyl-diethylferrocene, 5,10-dimethyl-5,10-dihydrophenazine (DMP), 3,7,10-trimethylphenothiazine, 2,3,7,8-tetramethoxy-thianthrene, 10-methylphenothiazine, tetramethylphenazine (TMP), bis(butyltriethylammonium)-para-methoxytriphenodithiazine (TPDT), 3,10-dimethoxy-7,14-(triethylammoniumbutyl)-triphenodithazinebis(tetrafluoroborate), and combinations thereof. Additional examples of anodic components that can be used in combination with the substituted ketal phenazines of the present disclosure include a substituted or unsubstituted 2,7-dialkyl-5,10-dialkyl-5,10-dihydrophenazine compound. In another example, at least one alkyl group of the 5,10-dialkyl groups attached to the phenazine compound includes at least 4 carbon atoms and is void of any β hydrogen atoms, and at least one alkyl group of the 2,7-dialkyl groups attached to the phenazine compound includes at least 4 carbons. In another example, at least one alkyl group of the 5,10-dialkyl groups attached to the phenazine compound includes a substituted or unsubstituted neopentyl group, and at least one alkyl group of the 2,7-dialkyl groups attached to the phenazine compound includes a substituted or unsubstituted isopropyl, isobutyl, (2-ethylbutyl), or (2-propylpentyl) group. In another example, at least one alkyl group of the 5,10-dialkyl groups attached to the phenazine compound includes a neopentyl group, and at least one alkyl group of the 2,7-dialkyl groups attached to the phenazine compound includes a 2-ethyl-1-butanol group. In yet another example, at least one alkyl group of the 5,10-dialkyl groups attached to the phenazine compound includes a neopentyl group, and at least one alkyl group of the 2,7-dialkyl groups attached to the phenazine compound includes an isobutyl group. The one or more additional anodic components may be incorporated into a polymeric film to form an anodic film in a manner similar to that described above with respect to the substituted ketal phenazines of the present disclosure. The one or more additional anodic components can be incorporated into the backbone of the polymeric chains forming the polymeric film and/or covalently bonded to the polymeric chains as pendant groups. The substituted ketal phenazines of the present disclosure and the one or more additional anodic components can be incorporated into the same polymeric film or separate polymeric films.

The cathodic component of the electrochromic medium can be any suitable solvent, film, or gel-based material having a cathodic component incorporated therein capable of cooperating with the substituted ketal phenazine compounds of Formula (I) to form an electro-optic element. The cathodic component can include a reducible compound, non-limiting examples of which include a viologen, a low-dimerizing viologen, or a non-dimerizing viologen. Illustrative viologens include, but are not limited to, methyl viologen, octyl viologen, benzyl viologen, polymeric viologens, and the viologens described in U.S. Pat. Nos. 4,902,108; 6,188,505; 5,998,617; 9,964,828; and 6,710,906, which are herein incorporated by reference in their entirety. In one aspect, the cathodic component is selected from a viologen, a low-dimerizing viologen, a non-dimerizing viologen, a substituted viologen, a di-acrylate viologen, a cathodic di-vinyl viologen, a cathodic di-vinyl ether viologen, a cathodic di-epoxy viologen, a cathodic di-oxetane viologen, a cathodic di-hydroxy viologen, or a combination thereof. The cathodic component may be incorporated into a polymeric film to form a cathodic film. The cathodic component can be incorporated into the backbone of the polymeric chains forming the polymeric film and/or covalently bonded to the polymeric chains as pendant groups in a manner similar to that described above with respect to the anodic film. In some examples, the electrochromic medium may include a combination of two or more cathodic components to provide the electrochromic medium with the desired color when activated. Examples of suitable combinations of anodic and cathodic components can be found in U.S. Pat. No. 6,020,987, entitled "Electrochromic Medium Capable of Producing a Pre-Selected Color," issued Feb. 1, 2000, the contents of which are incorporated herein by reference in their entirety.

Without being limited by any theory, it is believed that immobilizing the anodic components and the cathodic components, such as by incorporating the anodic components and cathodic components into a polymeric matrix, inhibits the activated anodic and activated cathodic components from undergoing charge transfer processes that may lead to clearing of the electrochromic device. Typically, upon charging of a traditional solution-phase electrochromic device, internal diffusion processes may result in charge transfer reactions that result in clearing of the device upon removal of the electric potential. Immobilizing the anodic components and the cathodic components can result in the electrochromic device maintaining its darkened (colored) state for longer periods of time upon removal of the electric potential compared to a solution phase device incorporating the same anodic and cathodic components.

According to some aspects, a concentration of the substitute ketal phenazine compounds of Formula (I), the one or more additional anodic components, and/or the cathodic component in the electrochromic medium can be from about 1 millimolar (mM) to about 500 mM, from about 2 mM to about 100 mM, about 5 mM to about 50 mM, about 40 mM to about 50 mM, about 60 mM to about 90 mM, or about 70 mM to about 80 mM. In one aspect, a concentration of the cathodic component is about 50 mM, about 50 mM to about 100 mM, about 60 to about 90 mM, or about 70 mM to about 80 mM. In one aspect, a concentration of any of the anodic components present in the electrochromic medium is at least 5 mM or about 2 mM to about 100 mM, about 5 mM to about 50 mM, or about 7 mM to about 50 mM. When more than one anodic component is present, a concentration of each of the anodic components may be determined individually.

The electrochromic medium may also include an electrolyte, which may be in the form of a solvent and a salt. The salt may be a metal salt or an ammonium salt. Non-limiting examples of suitable solvents for use in the electrolyte include: 3-methylsulfolane, dimethyl sulfoxide, dimethyl formamide, tetraglyme, and other polyethers; alcohols such as ethoxyethanol; nitriles, such as acetonitrile, glutaronitrile, 3-hydroxypropionitrile, and 2-methylglutaronitrile; ketones including 2-acetylbutyrolactone, and cyclopentanone; cyclic esters including beta-propiolactone, gamma-butyrolactone, and gamma-valerolactone; propylene carbonate (PC), ethylene carbonate; and homogenous mixtures thereof. Non-limiting examples of suitable salts include: metal or ammonium salts, such as $Li^+$, $Na^+$, $K^+$, $NR'_4{}^+$ (where each R' is individually H, alkyl, or cycloalkyl), of the following anions $F^-$, $Cl^-$, $Br^-$, $I^-$, $BF_4{}^-$, $PF_6{}^-$, $SbF_6{}^-$, $AsF_6{}^-$, $ClO_4{}^-$, $SO_3CF_3{}^-$, $N(CF_3SO_2)_2{}^-$, $C(CF_3SO_2)_3{}^-$, $N(SO_2C_2F_5)^-$, $Al(OC(CF_3)_3)_4{}^-$, or $BAr_4{}^-$, wherein Ar is an aryl or fluorinated aryl group such as, but not limited to, $C_6H_5$, 3,5-$(CF_3)_2C_6H_3$, or $C_6F_5$.

The electrochromic medium may optionally include additional materials, such as light absorbers, light stabilizers, thermal stabilizers, antioxidants, oxygen scavengers, thickeners, viscosity modifiers, tint providing agents, redox buffers, and mixtures of any two or more such materials. Non-limiting examples of UV-stabilizers may include ethyl-2-cyano-3,3-diphenyl acrylate; (2-ethylhexyl)-2-cyano-3,3-diphenyl acrylate; 2-(2'-hydroxy-4'-methylphenyl)benzotriazole, sold by Ciba-Geigy Corp. under the trademark Tinuvin® P; 3-[3-(2H-benzotriazole-2-yl)-5-(1,1-dimethylethyl)-4-hydroxyphenyl]propionic acid pentyl ester prepared from Tinuvin® 213, sold by Ciba-Geigy Corp., via conventional hydrolysis followed by conventional esterification (hereinafter "Tinuvin® PE"); 2,4-dihydroxybenzophenone; 2-hydroxy-4-methoxybenzophenone; and 2-ethyl-2'-ethoxyalanilide.

Figure 2A:
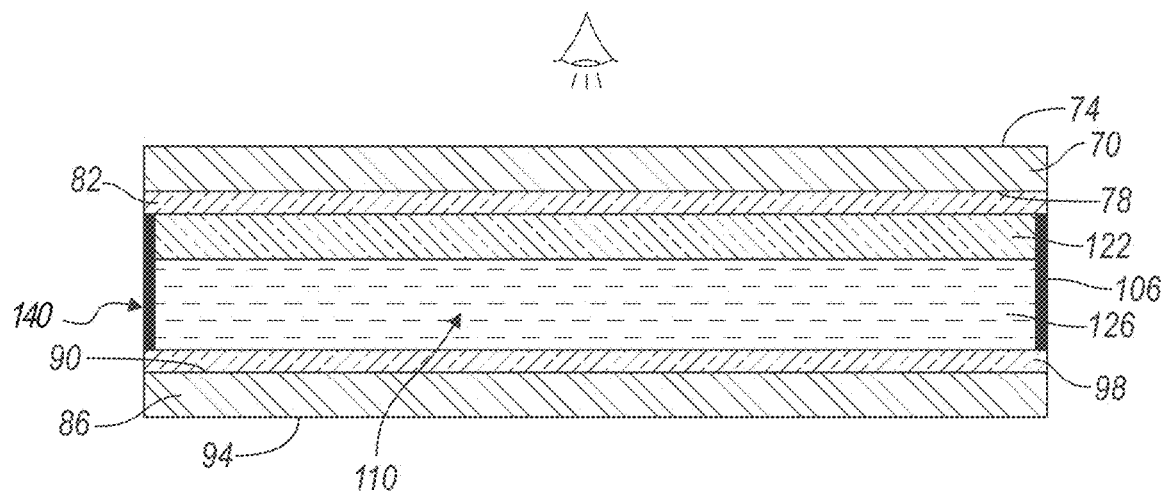
FIG. 2A is a cross-sectional schematic view of an electro-optic element, according to an aspect of the present disclosure.
Figure 2B:
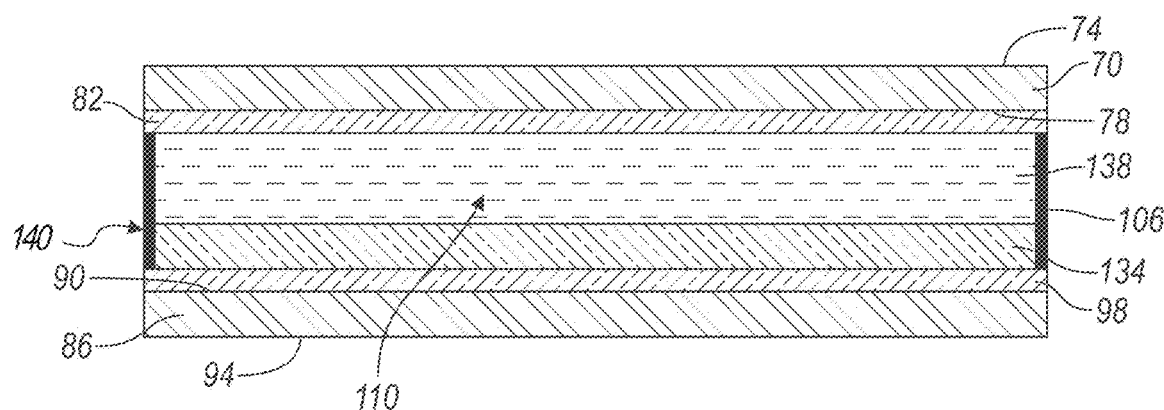
FIG. 2B is a cross-sectional schematic view of an electro-optic element, according to an aspect of the present disclosure.
Figure 2C:
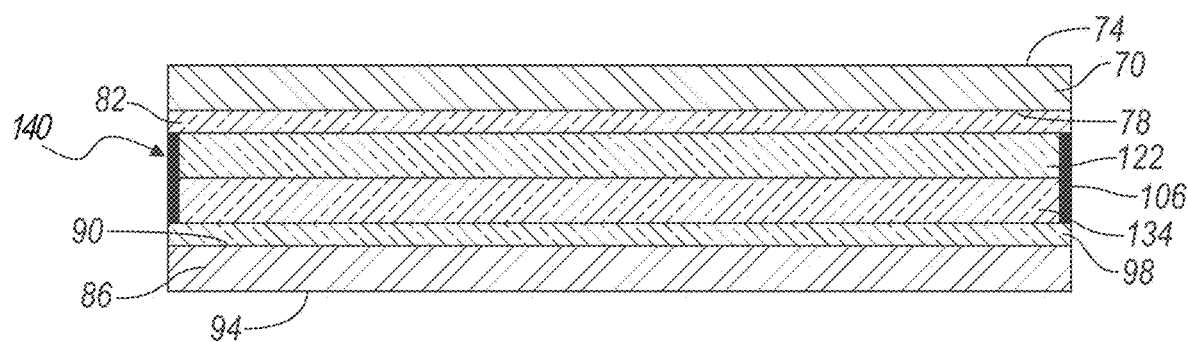
FIG. 2C is a cross-sectional schematic view of an electro-optic element, according to an aspect of the present disclosure.
Figure 2D:
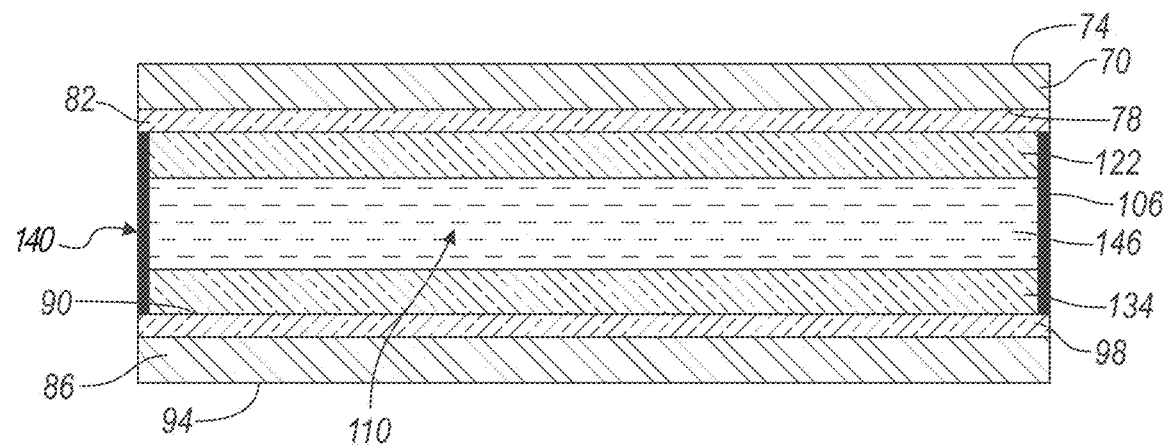
FIG. 2D is a cross-sectional schematic view of an electro-optic element, according to an aspect of the present disclosure.

FIGS. 2A, 2C, and 2D illustrate exemplary configurations of the electro-optic element 140 including a cathodic film 122 wherein the cathodic component is covalently bound into the film. As illustrated in FIG. 2A, the cathodic film 122 can be utilized in an electro-optic element 140 in combination with an anodic solution or gel 126 including the substituted ketal phenazine anodic component according to Formula (I) and optionally at least one additional anodic component. The cathodic film 122 can be disposed on the first electrically conductive layer 82 while the anodic solution or gel 126 can be disposed on the second electrically conductive layer 98. Optionally, the relative locations of the cathodic film 122 and the anodic solution or gel 126 can be reversed.

Additionally, the anodic solution or gel 126 may contain one or more electrolytes configured to facilitate electrical communication of the first and second electrically conductive layers 82, 98 across the anodic solution or gel 126 and cathodic film 122. The anodic solution or gel 126 may be in a semi-liquid state capable of ionically transporting the anodic component to the cathodic component within the cathodic film 122. For example, the anodic solution or gel 126 may permeate the cathodic film 122 with the one or more electrolytes and/or anodic components.

FIG. 2B illustrates an exemplary configuration of the electro-optic element 140 including a cathodic solution or gel 138. As illustrated in FIG. 2B, the cathodic solution or gel 138 can be utilized in the electro-optic element 140 with an anodic film 134, as illustrated in FIGS. 2B-D. The cathodic solution or gel 138 can be disposed on the first electrically conductive layer 82, while the anodic film 134 can be disposed on the second electrically conductive layer 98, or vice versa. The cathodic solution or gel 138 can be an electrochromic gel that may contain one or more electrolytes configured to facilitate electrical communication of the first and second electrically conductive layers 82, 98 across the cathodic solution or gel 138 and anodic film 134. According to one aspect, the cathodic solution or gel 138 may be in a semi-liquid state capable of ionically transporting the cathodic component to the anodic component within the anodic film 134. For example, the cathodic solution or gel 138 may permeate the anodic film 134 with the one or more electrolytes and/or cathodic components. In the depicted example, either or both of the anodic and cathodic components of the anodic film 134 and cathodic solution or gel 138, respectively, may be electrochromic.

The anodic film 134 can be any suitable film incorporating the substituted ketal phenazine anodic component according to Formula (I) and optionally at least one additional anodic component. In examples of the of the electro-optic element 140 including the anodic film 134, the substituted ketal phenazine anodic component according to Formula (I) and the optional at least one additional anodic component may be disposed between the monomer units of the backbone and/or present as pendant groups on the polymer chain.

Referring now to the example depicted in FIG. 2C, the electro-optic element 140 includes both the cathodic film 122 and the anodic film 134. The cathodic film 122 and the anodic film 134 may be in direct contact with one another, or may be separated (e.g., by a film which is configured to promote electrical isolation or ion exchange). As explained above, the cathodic and anodic films 122, 134 may be polymeric films including the cathodic component and anodic component disposed along the backbone, or as pendant groups, of the polymeric chains of the cathodic and anodic films 122, 134, respectively.

Referring now to the example depicted in FIG. 2D, the electro-optic element 140 includes both the cathodic film 122 and the anodic film 134 in addition to an electrolyte layer 146 separating the films 122, 134. The electrolyte layer 146 may be a gel (e.g., a semi-liquid configured to permeate the cathodic and anodic films 122, 134) or polymeric electrolyte. In examples utilizing a polymeric electrolyte as the electrolyte layer 146, the polymeric electrolyte may include poly(styrene-ran-ethylene), polystyrene-block-poly(ethylene-ran-butylene), poly(styrene-ran-ethylene), polystyrene-block-poly(ethylene/butylene)-block-polystyrene, poly(ethylene glycol), poly(methyl methacrylate), other polymer electrolytes and/or combinations thereof. The electrolyte layer 146 may partially permeate the cathodic and anodic films 122, 134.

Figure 2E:
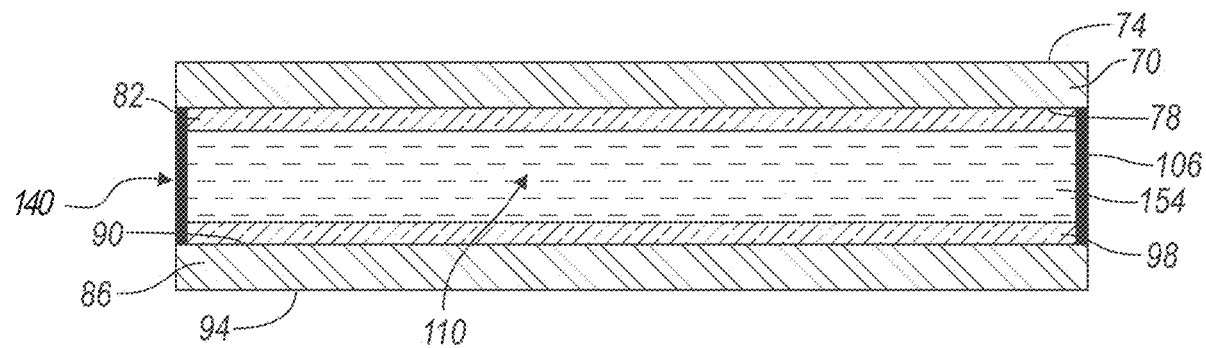
FIG. 2E is a cross-sectional schematic view of an electro-optic element, according to an aspect of the present disclosure.

Referring now to the example depicted in FIG. 2E, the electro-optic element 140 may include an electro-optic film 154. The electro-optic film 154 may be a polymeric material composed of a plurality of polymeric chains, similar to the cathodic and anodic films 122, 134 (FIGS. 2C and 2D). In such an example, the electro-optic film 154 may contain both the anodic component and the cathodic component on the backbones of the polymeric chains, and/or as pendant groups. In some examples, the anodic component and cathodic component may both be positioned on the same polymer chains, while in other examples, the anodic component and cathodic component may be positioned on separate polymeric chains. Alternatively, the electro-optic film 154 may be a solution or a gel that contains both anodic and cathodic materials not bound to a polymer, but free to diffuse through the electro-optic film 154.

The substituted ketal phenazines of the present disclosure may be utilized in electrochromic mediums for electro-optic elements that may be utilized in a variety of different electrochromic devices, non-limiting examples of which include interior and exterior mirror assemblies, interior and exterior windows, display screens, heads-up displays, vehicle window assemblies, architectural window assemblies, filter assemblies, eye wear, cameras, and display boards.

The following examples describe various features and advantages provided by the disclosure, and are in no way intended to limit the invention and appended claims.

EXAMPLES

Example 1

Figure 4:
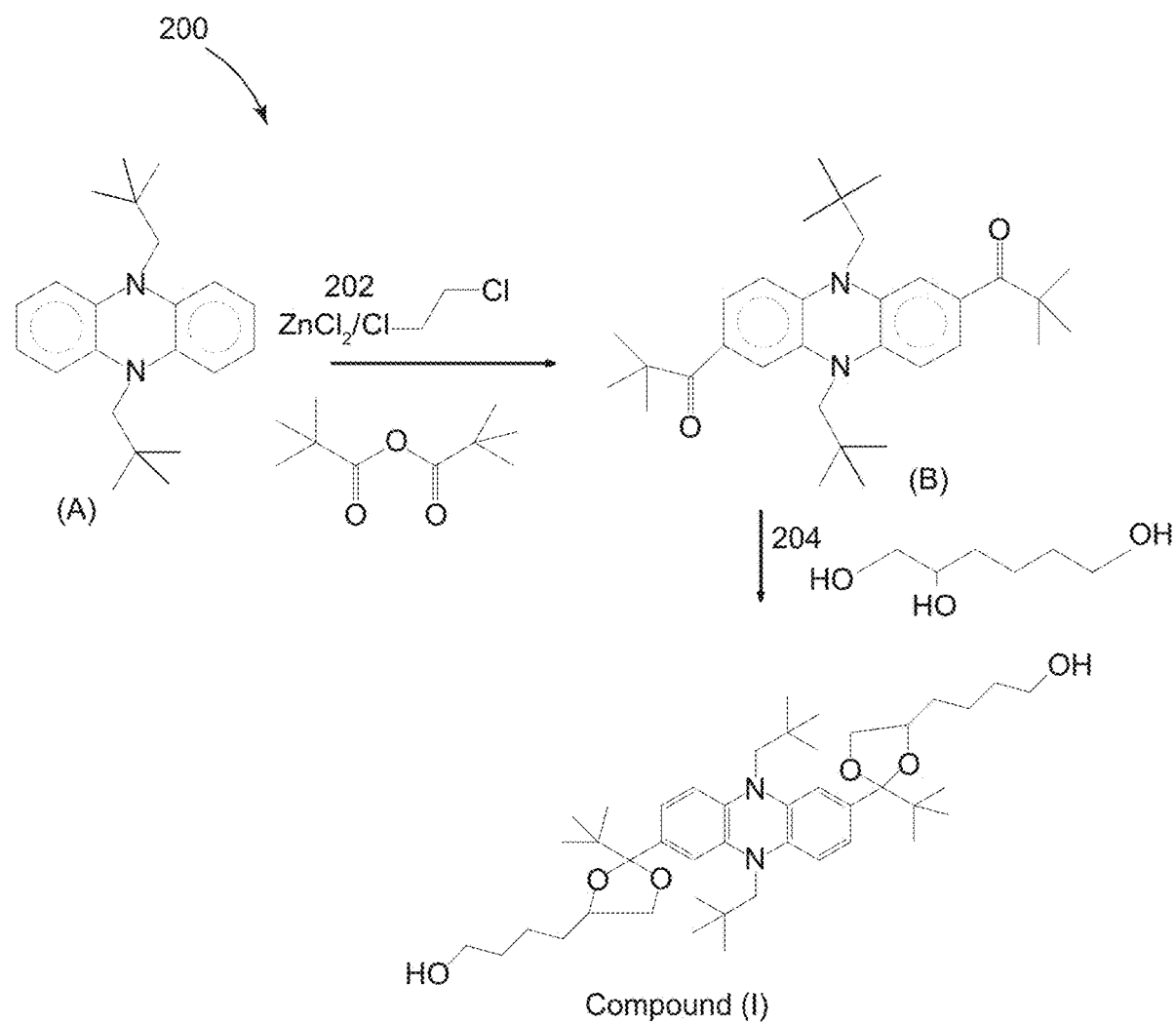
FIG. 4 is a flow chart depicting a synthetic scheme for synthesizing an exemplary electrochromic compound, according to an aspect of the present disclosure.

FIG. 4 illustrates an exemplary synthetic scheme 200 for synthesizing the substituted ketal phenazine Compound (I) of FIG. 3A. While the synthesis is discussed in the context of Compound (I), it is understood that the synthesis process is applicable to other substituted ketal phenazines of Formula (I). It is also understood that Compound (I) may synthesized according to other processes. It is also understood that the synthetic scheme 200 may include additional or alternative steps without deviating from the scope of the present disclosure.

Still referring to FIG. 4, step 202 is a Friedel-Crafts diacylation of 5,10-dineopentyl-5,10-dihydrophenazine (A) to produce 2,7-trimethyl acetyl-5,10-dineopentyl-5,10-dihydrophenazine (B). It is possible to form a mixture of isomers at this step, for example diacylation at the 2,6 positions, the 2,8 positions, and the 2,9 positions. At step 202, 25 grams of 5,10-dineopentyl-5,10-dihydrophenazine, 4.36 grams of zinc chloride, 43.3 grams of pivalic anhydride, and 300 milliliters (ml) dichloroethane were charged in a 1 liter reaction flask and heated to reflux for 15 hours. The reaction mixture was then cooled to room temperature. 200 ml of a 1 Normal dilute hydrochloric acid solution was slowly added to the reaction mixture. The reaction mixture was then heated to 70° C. for four hours and then cooled to room temperature. The reaction mixture was transferred to separatory funnel, the aqueous layer was removed, and the organic layer was transferred to a reaction flask. To this reaction flask, 150 ml of water and 10 ml of 50% sodium hydroxide solution was added and the mixture was stirred for 4 hours. The reaction mixture was transferred to a separatory funnel and the organic layer was separated. Solvent was distilled off to give a solid which was recrystallized from 100 ml hexane to give 25.8 g of 2,7-trimethyl acetyl-5,10-dineopentyl-5,10-dihydrophenazine (B).

5,10-dineopentyl-5,10-dihydrophenazine can be synthesized as described in Examples 2 and 3 of U.S. Pat. No. 7,428,091, issued Sep. 23, 2008 and entitled "Electrochromic Compounds and Associated Media and Devices", the contents of which are incorporated herein by reference in their entirety.

At step 204, 2,7-trimethyl acetyl-5,10-dineopentyl-5,10-dihydrophenazine (B) is reacted with 1,2,6-hexanetriol in an acid catalyzed ketalization process to form 4-(2-tert-butyl-2-{7-[2-tert-butyl-4-(4-hydroxylbutyl)-1,3-dioxolan-2-yl}-5,10-bis(2,2-dimethylpropyl) phenazine-2-yl)-1,3-dioxolan-4-yl}butane-1-ol (Compound (I)). Step 204 involves charging 10 grams of 2,7-trimethyl acetyl-5,10-dineopentyl-5,10-dihydrophenazine, 10 grams of 1,2,6-hexane triol, 0.3 grams of p-toluene sulfonic acid, and 300 ml toluene to a 500 ml 3-neck round bottom flask equipped with a Dean-Stark condenser. The reaction mixture was refluxed for 48 hours and then cooled to room temperature. To this reaction mixture, 100 ml of dilute sodium dithionite solution was added and the mixture was transferred to a separatory funnel. The organic layer was separated and solvent was removed to give an oil. To this oil 200 ml hexane was added and the mixture was cooled to 5° C. over night. The solid was filtered to yield about 8.9 gram of Compound (I).

Compound (II) of FIG. 3B can be synthesized using step 202 to generate trimethyl acetyl-5,10-dineopentyl-5,10-dihydrophenazine (B). Compound (II) can be produced from structure (B) by charging 3 grams of 2,7-trimethyl acetyl-5,10-dineopentyl-5,10-dihydrophenazine (B), 8.3 grams of anhydrous glycerol, 0.2 grams of p-toluene sulfonic acid, and 150 ml toluene to a 250 ml 3-neck round bottom flask equipped with a Dean-Stark condenser. The reaction mixture was refluxed for 72 hours and then cooled to room temperature. To this mixture, 100 ml of dilute sodium dithionite solution was added and the mixture was transferred to a reparatory funnel. The solvent was removed to yield about 3.5 gram of 4-(2-tert-butyl-2-{7-[2-tert-butyl-4-(4-hydroxymethyl)-1,3-dioxolan-2-yl]-5,10-bis(2,2-dimethylpropyl) phenazine-2-yl}-1,3-dioxolan-4-yl) methanol (Compound (II)).

Example 2

Figure 5:
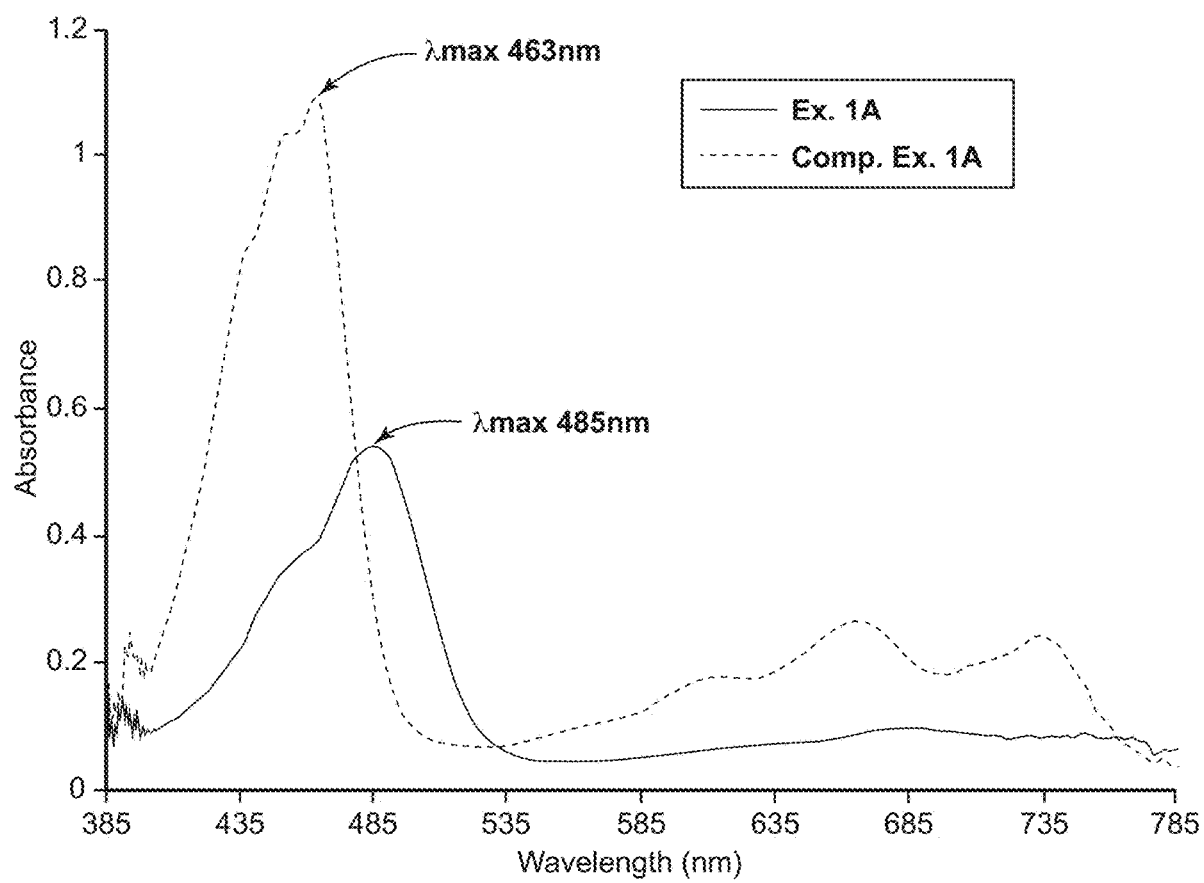
FIG. 5 is a plot of absorbance as a function of wavelength for an exemplary electrochromic compound according to an aspect of the present disclosure and a comparative electrochromic compound.

FIG. 5 is a plot comparing the absorbance of a radical cation of the exemplary substituted ketal phenazine Compound (I) of FIG. 3A and a radical cation of a comparative phenazine compound (Comparative Compound (I)) shown below:

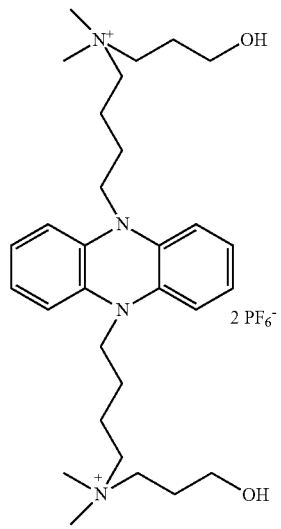

(Comparative Compound (I))

where $PF_6^-$ is a hexafluorophosphate counterion.

Figure 6:
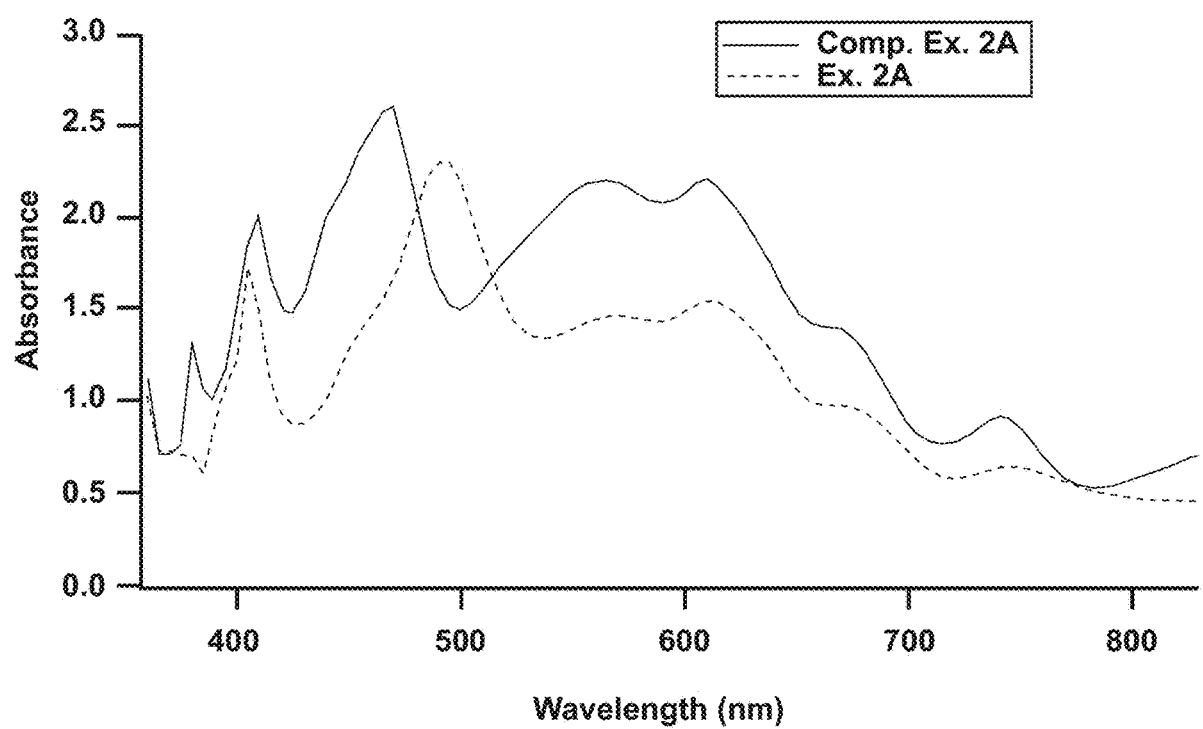
FIG. 6 is a plot of absorbance as a function of wavelength for an exemplary electrochromic device including an electrochromic compound according to an aspect of the present disclosure and a comparative electrochromic medium.
Figure 7:
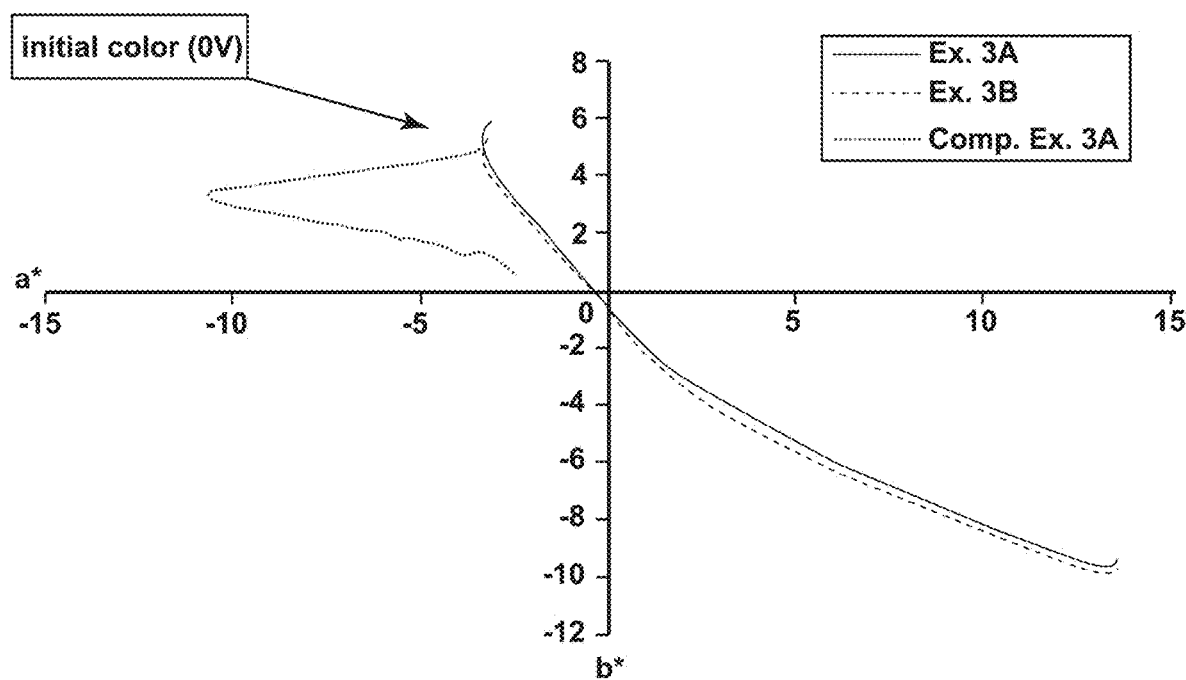
FIG. 7 is a plot of CIE LAB color space color values a* and b* of an electrochromic device as an applied potential is increased from 0 volts to 0.8 volts for a first and second exemplary electrochromic medium (Ex. 3A and Ex. 3B, respectively) according to an aspect of the present disclosure and a comparative electrochromic medium (Comp. Ex. 3A).

The experimental set-up for the sample electrochemical cell used to generate the data shown in FIGS. 6-7 is as follows:

A sample of Comparative Compound (I) ("Comparative Example 1A") was prepared by coating an indium tin oxide (ITO) coated piece of four 3"×3" glass sections (2.2 mm thickness) with a mixture made by dissolving 0.16 grams of bis (11-hydroxyundecyl) viologen bis[hexafluorophosphate] ($PF_6$), 0.186 grams of bis (6-hydroxyhexyl) viologen bis[bis trifluoromethanesulfonyl imide] (NTF), 0.0006 grams of surfactant (TEGO Glide 410), and 0.134 grams of HDT in a 3 gram solution in propylene carbonate (PC) and 3-methoxypropionitrile (MPN) (35% wt PC, 65% wt MPN), plus 20 microliters of a 0.6 percent by weight (% wt) solution of dibutyltin diacetate (DBTDA) catalyst in PC thereby forming a first film. This coating was made using a #16 Mayer rod to control thickness. A second piece of four 3"×3" glass sections (2.2 mm thickness) was coated with a solution made by dissolving 0.317 grams of phenazine, 0.001 grams of surfactant (TEGO Glide 450), and 0.133 grams of HDT in a 2 gram solution in propylene carbonate (PC) and 3-methoxypropionitrile (MPN) (35% wt PC, 65% wt MPN), plus 14 microliters of a 0.6% wt solution of DBTDA catalyst in PC, thereby forming a second film. This second film was made using a #8 Mayer rod to control thickness.

A sample of Compound (I) ("Example 1A") was prepared by coating an indium tin oxide (ITO) coated piece of four 3"×3" glass sections (2.2 mm thickness) with a mixture made by dissolving 0.16 grams of bis(11-hydroxy undecyl) viologen bis[hexafluorophosphate] ($PF_6$), 0.186 grams of bis (6-hydroxyhexyl)viologen bis[bistrifluoromethane sulfonyl imide] (NTF), 0.0006 grams of surfactant (TEGO Glide 410), and 0.134 grams of HDT in a 3 gram solution in propylene carbonate (PC) and 3-methoxypropionitrile (MPN) (35% PC, 65% MPN) plus 20 microliters of a 0.6% wt solution of dibutyl tin diacetate (DBTA) catalyst in PC, thereby forming the first film. This coating was made using #16 Mayer rod to control the thickness. A second piece of 3"×3" glass sections (2.2 mm thickness) was coated with a mixture made with a solution made by dissolving 0.209 grams of ketal phenazine Compound (I), 0.105 grams of N,N'-bis[dimethyl(2-propanol)]-1,6-hexyl ammonium di[bis (trifluoromethane sulfonamide)], 0.001 grams of surfactant (TEGO Glide 450), and 0.136 grams of HDT in 2 gram solution in 40% wt cyclohexanone, 30% wt diacetone alcohol, 20% wt ethylene glycol diacetate, and 10% wt butyl carbitol acetate, plus 34 microliters of DBTA in PC, thereby forming a second film. This second film was made with a #8 Mayer rod.

The films were allowed to cure under a nitrogen atmosphere overnight in an oven at 60° C. The first and second films on their respective glass substrates were positioned in a space-apart relationship facing each other and an epoxy seal was placed around the perimeter and cured to form a cell leaving offsets for attachment of electrical contacts. The distance between the two substrates was about 135 micrometers. The resulting cell was filled with a solution of 0.1 molar tetraethyl ammonium tetrafluoroborate (TEABF$_4$) and a cross-linkable polymer matrix precursor in PC to form a polymeric electrolyte.

The absorbance of a radical cation of Compound (I) (Example 1A) and a radical cation of Comparative Compound (I) (Comparative Example 1A) was measured over a working optical range of about 385 nm to about 785 nm. The radical cation of Compound (I) and Comparative Compound (I) represent the oxidized species that would be present in an electrochromic device utilizing these compounds as the anodic component. The radical cation for Example 1A and Comparative Example 1A was oxidized by applying a potential to the sample electrochemical cell formed as described above. The working electrode was a piece of glass with half-wave ITO coating, the reference electrode was a silver wire pseudo reference electrode, and the counter electrode was a platinum mesh. A Gamry interface 1010E potentiostat was used to apply a potential of +305 mV versus the silver wire pseudo reference electrode. A USB4000 spectrometer was used to collect the spectra.

Compound (I) exhibits a red shift in its maximum absorbance ($X_{max}$) compared to a maximum absorbance of Comparative Compound (I) of about 22 nm. The overlap in maximum absorbance exhibited by Compound (I) and Comparative Compound (I) indicates that these compounds could be used in combination as the anodic component in an electrochromic device to produce a color that is more gray (i.e., more neutral in appearance) than Comparative Compound (I) alone.

Example 3

FIG. 6 is a plot comparing the absorbance of an exemplary electrochromic device (Example 2A) and a comparative electrochromic device (Comparative Example 2A). Both devices include a similar structure and components, except that Example 2A includes the exemplary substituted ketal phenazine Compound (I) of FIG. 3A and the Comparative Example 2A includes the Comparative Compound (I) of Example 1. Both devices utilized a viologen cathodic component. The electrochemical cell set-up was similar to that described above for Example 1.

Example 2A ("Ex. 2A") and Comparative Example 2A ("Comp. Ex. 2A") demonstrate the ability of the ketal phenazines of the present disclosure to be used in an electrochromic device with a cathodic component and exhibit a maximum absorbance when activated that is red-shifted from a conventional anodic phenazine compound, such as Comparative Compound (I).

Example 4

FIG. 7 is a plot of CIE LAB color space color values a* and b* for exemplary examples Example 3A ("Ex. 3A") and Example 3B ("Ex. 3B") and a comparative example, Comparative Example 3A ("Comp. Ex. 3A"). Examples 3A and 3B and Comparative Example 3A were tested using the same electrochromic device structure and the same cathodic component. Examples 3A and 3B included the exemplary substituted ketal phenazine Compound (I) of FIG. 3A in 20% by mole diquatdiol and 30% by mole diquatdiol, respectively. Comparative Example 3A included the comparative anodic component, Comparative Compound (I) of Example 1. The electrochemical cell set-up was similar to that described above for Example 1.

The voltage applied to the test devices for Examples 3A and 3B and Comparative Example 3A was stepped from 0 volts to 0.8 volts and held at 0.8 volts for 5 min. The color space color values a* and b* were determined using a D65 illuminant and an AOI of 2 degrees. The plot for Comparative Example 3A (Comp. Ex. 3A) shows that the observed color stays within the greenish-yellowish quadrant of the color space, when activated. However, Examples 3A and 3B (Ex. 3A and Ex. 3B) show an observed color that shifts into the red-blue quadrant of the color space, when activated.

Additional aspects of the present disclosure include:

According to a first aspect of the present disclosure, an electro-optic element, includes: a first substrate defining first and second surfaces, wherein a first electrically conductive layer is disposed on the second surface; a second substrate defining third and fourth surfaces, wherein a second electrically conductive layer is disposed on the third surface; and an electrochromic medium disposed in a cavity between the first and second substrates, the electrochromic medium including an anodic component and a cathodic component; wherein at least the anodic component is configured to reversibly attenuate transmittance of light having a wavelength within a predetermined wavelength range when in an electrochemically activated state; and wherein the anodic component includes a compound of Formula (I):

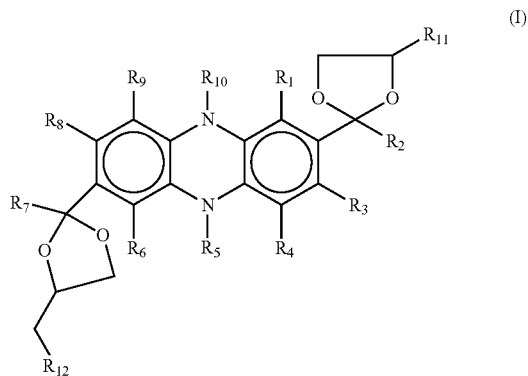

wherein $R_1$, $R_2$, $R_3$, $R_4$, $R_6$, $R_7$, $R_8$, $R_9$, $R_{11}$, and $R_{12}$ are individually a hydrogen, alkyl, substituted alkyl, straight chain alkyl, branched alkyl, or cycloalkyl and $R_5$ and $R_{10}$ are individually an alkyl, substituted alkyl, straight chain alkyl, branched alkyl, or cycloalkyl.

According to the first aspect of the present disclosure, in a second aspect, wherein one of: $R_5$ and $R_{10}$; $R_{11}$ and $R_{12}$; or $R_5$, $R_{10}$, $R_{11}$, and $R_{12}$, individually comprise an alkyl, substituted alkyl, straight chain alkyl, branched alkyl, or cycloalkyl substituted with at least one polymerizable functional group.

According to the second aspect of the present disclosure, in a third aspect, wherein the polymerizable functional group includes at least one group selected from a vinyl group, acrylate group, methacrylate group, vinyl ether group, hydroxyl group, isocyanate group, oxetane group, amine group, and epoxy group.

According to the first aspect of the present disclosure, in a fourth aspect, wherein at least one of $R_2$, $R_5$, $R_7$, and $R_{10}$ are free of beta hydrogens.

According to the fourth aspect of the present disclosure, in a fifth aspect, wherein at least one of $R_2$, $R_5$, $R_7$, and $R_{10}$ includes one of a neopentyl group and tertiary alkyl.

According to the first aspect of the present disclosure, in a sixth aspect, wherein the anodic component includes at least one material selected from 4-(2-tert-butyl-2-{7-[2-tert-butyl-4-(4-hydroxylbutyl)-1,3-dioxolan-2-yl]-5,10-bis(2,2-dimethylpropyl) phenazine-2-yl)-1,3-dioxolan-4-yl}butane-1-ol (Compound (I)) and 4-(2-tert-butyl-2-{7-[2-tert-butyl-4-(4-hydroxymethyl)-1,3-dioxolan-2-yl]-5,10-bis(2,2-dimethylpropyl) phenazine-2-yl}-1,3-dioxolan-4-yl) methanol (Compound (II)):

Compound (I)

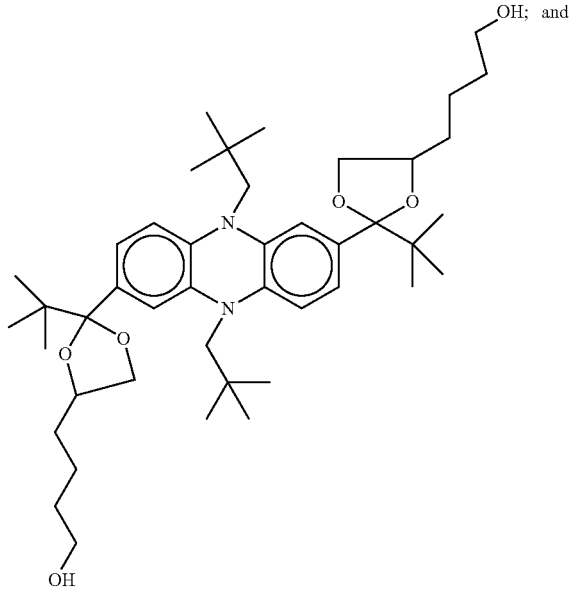

-continued

Compound (II)

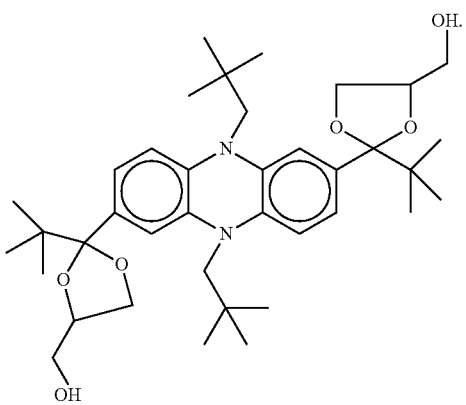

According to any one of the first to the fifth aspects of the present disclosure, in a seventh aspect, wherein the anodic component further includes at least one additional anodic compound, and wherein: the compound of Formula (I) includes a maximum absorption in a wavelength range of 400 nm to 550 nm, when in an electrochemically activated state; and the at least one additional anodic compound includes a maximum absorption in a wavelength range of 400 nm to 550 nm, when in an electrochemically activated state; wherein the maximum absorption of the compound of Formula (I) is within ±50 nm of the maximum absorption of the at least one additional anodic compound, when the compound of Formula (I) and the at least one additional anodic compound are in an electrochemically activated state.

According to the first seventh of the present disclosure, in an eighth aspect, wherein the compound of Formula (I) includes an oxidation potential and the at least one additional anodic compound includes an oxidation potential, and wherein: the oxidation potential of the compound of Formula (I) is within ±60 millivolts of the oxidation potential of the at least one additional anodic compound.

According to the seventh aspect of the present disclosure, in a ninth aspect, wherein the at least one additional anodic compound includes at least one material selected from metallocenes, 5,10-dihydrophenazines, phenothiazines, phenoxazines, carbazoles, triphenodithiazines, triphendioxazines, ferrocene, substituted ferrocenes, substituted ferrocenyl salts, phenazine, substituted phenazines, phenothiazine, substituted phenothiazines, including substituted dithiazines, thianthrene and substituted thianthrenes, di-tert-butyl-diethylferrocene, 5,10-dimethyl-5,10-dihydrophenazine (DMP), 3,7,10-trimethylphenothiazine, 2,3,7,8-tetramethoxy-thianthrene, 10-methylphenothiazine, tetramethylphenazine (TMP), bis(butyltriethylammonium)-para-methoxytriphenodithiazine (TPDT), 3,10-dimethoxy-7,14-(triethylammoniumbutyl)-triphenodithazinebis (tetrafluoroborate), and combinations thereof.

According to any one of the first to the ninth aspects of the present disclosure, in a tenth aspect, wherein the cathodic component includes at least one material selected from a viologen, low-dimerizing viologen, non-dimerizing viologen, substituted viologen, di-acrylate viologen, cathodic di-vinyl viologen, cathodic di-vinyl ether viologen, cathodic di-epoxy viologen, cathodic di-oxetane viologen, cathodic di-hydroxy viologen, and combinations thereof. According to any one of the first to the tenth aspects of the present disclosure, in an eleventh aspect, wherein the anodic component is one of dissolved in a solvent, incorporated into a gel, or incorporated into a polymeric film.

According to a twelfth aspect of the present disclosure, a medium for an electro-optic element, includes: an anodic component configured to reversibly attenuate transmittance of light having a wavelength within a predetermined wavelength range when in an electrochemically activated state, and wherein the anodic component includes a compound of Formula (I):

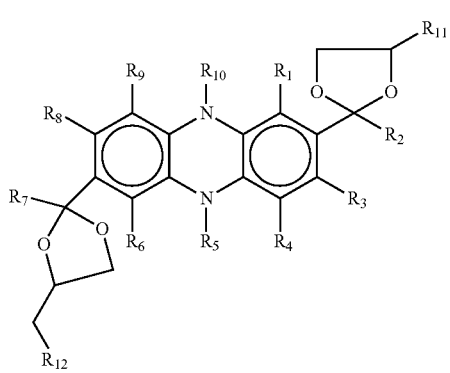

wherein $R_1$, $R_2$, $R_3$, $R_4$, $R_6$, $R_7$, $R_8$, $R_9$, $R_{11}$, and $R_{12}$ are individually a hydrogen, alkyl, substituted alkyl, straight chain alkyl, branched alkyl, or cycloalkyl and $R_5$ and $R_{10}$ are individually an alkyl, substituted alkyl, straight chain alkyl, branched alkyl, or cycloalkyl.

According to twelfth of the present disclosure, in a thirteenth aspect, wherein one of: $R_5$ and $R_{10}$; $R_{11}$ and $R_{12}$; or $R_5$, $R_{10}$, $R_{11}$, and $R_{12}$, individually comprise an alkyl, a substituted alkyl, straight chain alkyl, branched alkyl, or cycloalkyl substituted with at least one polymerizable functional group.

According to the thirteenth aspect of the present disclosure, in a fourteenth aspect, wherein the polymerizable functional group includes at least one group selected from a vinyl group, acrylate group, methacrylate group, vinyl ether group, hydroxyl group, isocyanate group, oxetane group, amine group, and epoxy group.

According to the twelfth of the present disclosure, in a fifteenth aspect, wherein at least one of $R_2$, $R_5$, $R_7$, and $R_{10}$ are free of beta hydrogens.

According to the fifteenth of the present disclosure, in a sixteenth aspect, wherein at least one of $R_2$, $R_5$, $R_7$, and $R_{10}$ includes one of a neopentyl group and tertiary alkyl.

According to the twelfth of the present disclosure, in a seventeenth aspect, wherein the anodic component includes at least one material selected from 4-(2-tert-butyl-2-{7-[2-tert-butyl-4-(4-hydroxylbutyl)-1,3-dioxolan-2-yl]-5,10-bis (2,2-dimethylpropyl) phenazine-2-yl)-1,3-dioxolan-4-yl}butane-1-ol (Compound (I)) and 4-(2-tert-butyl-2-{7-[2-tert-butyl-4-(4-hydroxymethyl)-1,3-dioxolan-2-yl]-5,10-bis (2,2-dimethylpropyl) phenazine-2-yl}-1,3-dioxolan-4-yl) methanol (Compound (II)):

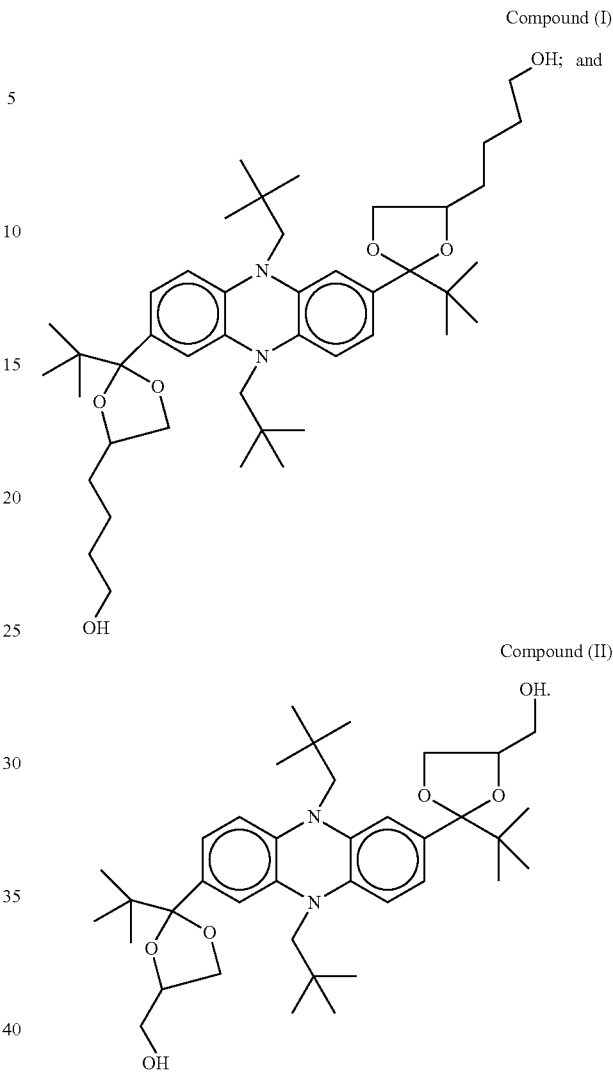

According to the twelfth of the present disclosure, in an eighteenth aspect, wherein the anodic component further includes at least one additional anodic compound, and wherein: the compound of Formula (I) includes a maximum absorption in a wavelength range of 400 nm to 550 nm, when in an electrochemically activated state; and the at least one additional anodic compound includes a maximum absorption in a wavelength range of 400 nm to 550 nm, when in an electrochemically activated state; wherein the maximum absorption of the compound of Formula (I) is within ±50 nm of the maximum absorption of the at least one additional anodic compound, when the compound of Formula (I) and the additional anodic compound are in an electrochemically activated state.

According to the eighteenth of the present disclosure, in a nineteenth aspect, wherein the compound of Formula (I) includes an oxidation potential and the at least one additional anodic compound includes an oxidation potential, and wherein: the oxidation potential of the compound of Formula (I) is within ±60 millivolts of the oxidation potential of the at least one additional anodic compound.

According to the nineteenth of the present disclosure, in a twentieth aspect, wherein the at least one additional anodic compound includes at least one material selected from metallocenes, 5,10-dihydrophenazines, phenothiazines, phenoxazines, carbazoles, triphenodithiazines, triphendioxazines, ferrocene, substituted ferrocenes, substituted ferrocenyl salts, phenazine, substituted phenazines, phenothiazine, substituted phenothiazines, including substituted dithiazines, thianthrene and substituted thianthrenes, di-tert-butyl-diethylferrocene, 5,10-dimethyl-5,10-dihydrophenazine (DMP), 3,7,10-trimethylphenothiazine, 2,3,7,8-tetramethoxy-thianthrene, 10-methylphenothiazine, tetramethylphenazine (TMP), bis(butyltriethylammonium)-para-methoxytriphenodithiazine (TPDT), 3,10-dimethoxy-7,14-(triethylammoniumbutyl)-triphenodithazinebis (tetrafluoroborate), and combinations thereof.

According to any one of the twelfth to the twentieth aspects of the present disclosure, in a twenty-first aspect, wherein the anodic component is one of dissolved in a solvent, incorporated into a gel, or incorporated into a polymeric film.

It will be understood by one having ordinary skill in the art that construction of the described disclosure and other components is not limited to any specific material. Other exemplary embodiments of the disclosure disclosed herein may be formed from a wide variety of materials, unless described otherwise herein.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

What is claimed is:

1. An electro-optic element, comprising:
a first substrate defining first and second surfaces, wherein a first electrically conductive layer is disposed on the second surface;
a second substrate defining third and fourth surfaces, wherein a second electrically conductive layer is disposed on the third surface; and
an electrochromic medium disposed in a cavity between the first and second substrates, the electrochromic medium including an anodic component and a cathodic component;
wherein at least the anodic component is configured to reversibly attenuate transmittance of light having a wavelength within a predetermined wavelength range when in an electrochemically activated state; and
wherein the anodic component comprises a compound of Formula (I):

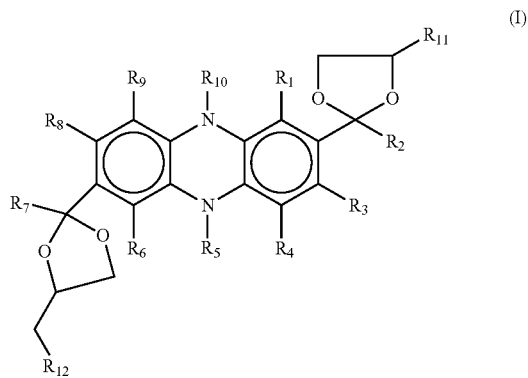

wherein $R_1$, $R_2$, $R_3$, $R_4$, $R_6$, $R_7$, $R_8$, $R_9$, $R_{11}$, and $R_{12}$ are individually a hydrogen, alkyl, substituted alkyl, straight chain alkyl, branched alkyl, or cycloalkyl and $R_5$ and $R_{10}$ are individually an alkyl, substituted alkyl, straight chain alkyl, branched alkyl, or cycloalkyl.

2. The electro-optic element of claim 1, wherein one of:
$R_5$ and $R_{10}$;
$R_{11}$ and $R_{12}$; or
$R_5$, $R_{10}$, $R_{11}$, and $R_{12}$,
individually comprise an alkyl, substituted alkyl, straight chain alkyl, branched alkyl, or cycloalkyl substituted with at least one polymerizable functional group.

3. The electro-optic element of claim 2, wherein the polymerizable functional group comprises at least one group selected from a vinyl group, acrylate group, methacrylate group, vinyl ether group, hydroxyl group, isocyanate group, oxetane group, amine group, and epoxy group.

4. The electro-optic element of claim 1, wherein at least one of $R_2$, $R_5$, $R_7$, and $R_{10}$ are free of beta hydrogens.

5. The electro-optic element of claim 4, wherein at least one of $R_2$, $R_5$, $R_7$, and $R_{10}$ comprises one of a neopentyl group and tertiary alkyl.

6. The electro-optic element of claim 1, wherein the anodic component comprises at least one material selected from 4-(2-tert-butyl-2-{7-[2-tert-butyl-4-(4-hydroxylbutyl)-1,3-dioxolan-2-yl]-5,10-bis(2,2-dimethylpropyl) phenazine-2-yl)-1,3-dioxolan-4-yl}butane-1-ol (Compound (I)) and 4-(2-tert-butyl-2-{7-[2-tert-butyl-4-(4-hydroxymethyl)-1,3-dioxolan-2-yl]-5,10-bis(2,2-dimethylpropyl) phenazine-2-yl}-1,3-dioxolan-4-yl) methanol (Compound (II)):

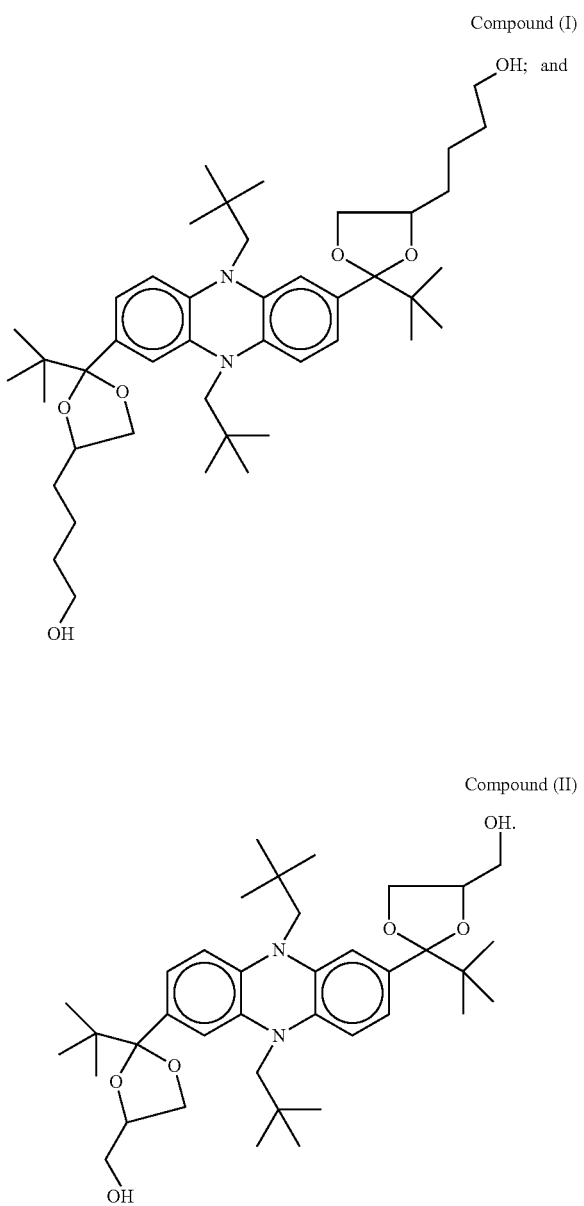

Compound (I)

Compound (II)

7. The electro-optic element of claim 1, wherein the anodic component further comprises at least one additional anodic compound, and wherein:
the compound of Formula (I) comprises a maximum absorption in a wavelength range of 400 nm to 550 nm, when in an electrochemically activated state; and
the at least one additional anodic compound comprises a maximum absorption in a wavelength range of 400 nm to 550 nm, when in an electrochemically activated state, and
wherein the maximum absorption of the compound of Formula (I) is within ±50 nm of the maximum absorption of the at least one additional anodic compound, when the compound of Formula (I) and the at least one additional anodic compound are in an electrochemically activated state.

8. The electro-optic element of claim 7, wherein the compound of Formula (I) comprises an oxidation potential and the at least one additional anodic compound comprises an oxidation potential, and wherein:
the oxidation potential of the compound of Formula (I) is within ±60 millivolts of the oxidation potential of the at least one additional anodic compound.

9. The electro-optic element of claim 7, wherein the at least one additional anodic compound comprises at least one material selected from metallocenes, 5,10-dihydrophenazines, phenothiazines, phenoxazines, carbazoles, triphenodithiazines, triphendioxazines, ferrocene, substituted ferrocenes, substituted ferrocenyl salts, phenazine, substituted phenazines, phenothiazine, substituted phenothiazines, including substituted dithiazines, thianthrene and substituted thianthrenes, di-tert-butyl-diethylferrocene, 5,10-dimethyl-5,10-dihydrophenazine (DMP), 3,7,10-trimethylphenothiazine, 2,3,7,8-tetramethoxy-thianthrene, 10-methylphenothiazine, tetramethylphenazine (TMP), bis(butyltriethylammonium)-para-methoxytriphenodithiazine (TPDT), 3,10-dimethoxy-7,14-(triethylammoniumbutyl)-triphenodithiazinebis(tetrafluoroborate), and combinations thereof.

10. The electro-optic element of claim 1, wherein the cathodic component comprises at least one material selected from a viologen, low-dimerizing viologen, non-dimerizing viologen, substituted viologen, di-acrylate viologen, cathodic di-vinyl viologen, cathodic di-vinyl ether viologen, cathodic di-epoxy viologen, cathodic di-oxetane viologen, cathodic di-hydroxy viologen, and combinations thereof.

11. The electro-optic element of claim 1, wherein the anodic component is one of dissolved in a solvent, incorporated into a gel, or incorporated into a polymeric film.

12. A medium for an electro-optic element, comprising:
an anodic component configured to reversibly attenuate transmittance of light having a wavelength within a predetermined wavelength range when in an electrochemically activated state, and
wherein the anodic component comprises a compound of Formula (I):

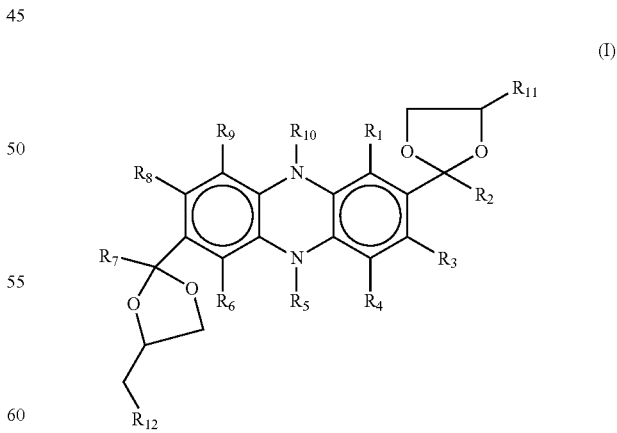

(I)

wherein $R_1$, $R_2$, $R_3$, $R_4$, $R_6$, $R_7$, $R_8$, $R_9$, $R_{11}$, and $R_{12}$ are individually a hydrogen, alkyl, substituted alkyl, straight chain alkyl, branched alkyl, or cycloalkyl and $R_5$ and $R_{10}$ are individually an alkyl, substituted alkyl, straight chain alkyl, branched alkyl, or cycloalkyl.

13. The medium of claim 12, wherein one of:

$R_5$ and $R_{10}$;

$R_{11}$ and $R_{12}$; or $R_5$, $R_{10}$, $R_{11}$, and $R_{12}$, individually comprise an alkyl, substituted alkyl, straight chain alkyl, branched alkyl, or cycloalkyl substituted with at least one polymerizable functional group.

14. The medium of claim 13, wherein the at least one polymerizable functional group comprises at least one group selected from a vinyl group, acrylate group, methacrylate group, vinyl ether group, hydroxyl group, isocyanate group, oxetane group, amine group, and epoxy group.

15. The medium of claim 12, wherein at least one of $R_2$, $R_5$, $R_7$, and $R_{10}$ are free of beta hydrogens.

16. The medium of claim 15, wherein at least one of $R_2$, $R_5$, $R_7$, and $R_{10}$ comprises one of a neopentyl group and tertiary alkyl.

17. The medium of claim 12, wherein the anodic component comprises at least one material selected from 4-(2-tert-butyl-2-{7-[2-tert-butyl-4-(4-hydroxylbutyl)-1,3-dioxolan-2-yl}-5,10-bis(2,2-dimethylpropyl) phenazine-2-yl)-1,3-dioxolan-4-yl}butane-1-ol (Compound (I)) and 4-(2-tert-butyl-2-{7-[2-tert-butyl-4-(4-hydroxymethyl)-1,3-dioxolan-2-yl]-5,10-bis(2,2-dimethylpropyl) phenazine-2-yl}-1,3-dioxolan-4-yl) methanol (Compound (II)):

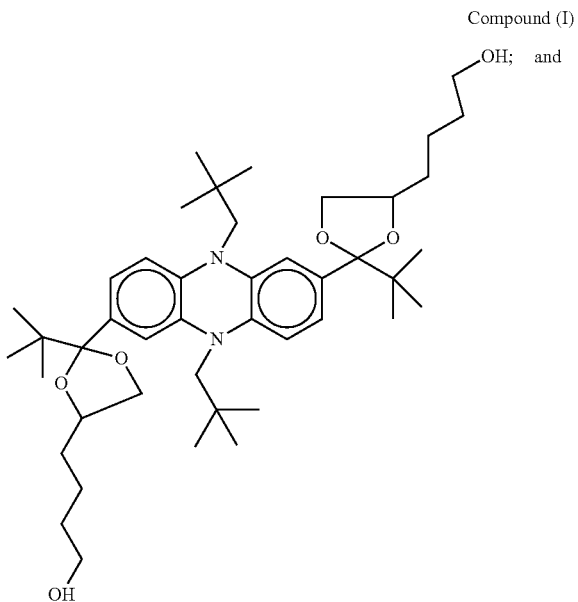

Compound (I)

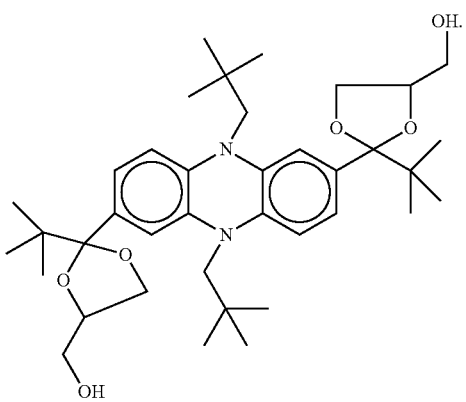

Compound (II)

18. The medium of claim 12, wherein the anodic component further comprises at least one additional anodic compound, and wherein:

the compound of Formula (I) comprises a maximum absorption in a wavelength range of 400 nm to 550 nm, when in an electrochemically activated state; and the at least one additional anodic compound comprises a maximum absorption in a wavelength range of 400 nm to 550 nm, when in an electrochemically activated state;

wherein the maximum absorption of the compound of Formula (I) is within ±50 nm of the maximum absorption of the at least one additional anodic compound, when the compound of Formula (I) and the additional anodic compound are in an electrochemically activated state.

19. The medium of claim 18, wherein the compound of Formula (I) comprises an oxidation potential and the at least one additional anodic compound comprises an oxidation potential, and wherein:

the oxidation potential of the compound of Formula (I) is within ±60 millivolts of the oxidation potential of the at least one additional anodic compound.

20. The medium of claim 19, wherein the at least one additional anodic compound comprises at least one material selected from metallocenes, 5,10-dihydrophenazines, phenothiazines, phenoxazines, carbazoles, triphenodithiazines, triphendioxazines, ferrocene, substituted ferrocenes, substituted ferrocenyl salts, phenazine, substituted phenazines, phenothiazine, substituted phenothiazines, including substituted dithiazines, thianthrene and substituted thianthrenes, di-tert-butyl-diethylferrocene, 5,10-dimethyl-5,10-dihydrophenazine (DMP), 3,7,10-trimethylphenothiazine, 2,3,7,8-tetramethoxy-thianthrene, 10-methylphenothiazine, tetramethylphenazine (TMP), bis(butyltriethylammonium)-para-methoxytriphenodithiazine (TPDT), 3,10-dimethoxy-7,14-(triethylammoniumbutyl)-triphenodithiazinebis (tetrafluoroborate), and combinations thereof.

* * * * *